US012558246B2

(12) United States Patent
Ducharme et al.

(10) Patent No.: US 12,558,246 B2
(45) Date of Patent: *Feb. 24, 2026

(54) LIVING HINGE FOR ATHLETIC BRACE OR SUPPORT

(71) Applicant: RUBBER CITY BRACING COMPANY LLC, Akron, OH (US)

(72) Inventors: Dustin Ducharme, Littleton, CO (US); Annunziato Amendola, Durham, NC (US); Bryan Den Hartog, Urbandale, IA (US); David B. Kay, Akron, OH (US); Anthony Perera, Cardiff (GB); Brian Milliff, Kirtland, OH (US); Patrick Brown, Cleveland Heights, OH (US)

(73) Assignee: Rubber City Bracing Company LLC, Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/773,526

(22) Filed: Jul. 15, 2024

(65) Prior Publication Data

US 2024/0398599 A1 Dec. 5, 2024

Related U.S. Application Data

(63) Continuation of application No. 17/510,006, filed on Oct. 25, 2021, now Pat. No. 12,036,141, which is a
(Continued)

(51) Int. Cl.
*A61F 5/01* (2006.01)

(52) U.S. Cl.
CPC .... *A61F 5/0127* (2013.01); *A61F 2005/0165* (2013.01)

(58) Field of Classification Search
CPC ........ A61F 5/01; A61F 5/0102; A61F 5/0104; A61F 5/0109; A61F 5/0111; A61F 5/0113; A61F 5/0123; A61F 5/0125; A61F 5/0127; A61F 5/0132; A61F 5/0134; A61F 5/0137; A61F 2005/0132; A61F 2005/0165;
(Continued)

(56) References Cited

U.S. PATENT DOCUMENTS 6,022,332 A 2/2000 Nelson
7,713,221 B1 5/2010 Weber et al.
(Continued)

*Primary Examiner* — Alireza Nia
*Assistant Examiner* — Gina McCarthy
(74) *Attorney, Agent, or Firm* — TILLMAN WRIGHT, PLLC; Chad D. Tillman

(57) ABSTRACT

A method of donning a rear-entry ankle brace includes positioning the brace on a mid-foot and a lower leg portion to span an ankle joint, with a distal end portion extending over a top and medial and lateral sides of the mid-foot, and with a proximal end extending over a front and medial and lateral sides of the lower leg portion; attaching leg straps in tension on a front of the brace; and extending a foot strap from a first end under the brace so as to define a plantar surface of the brace and further extending the foot strap over a front of an intermediate portion to the medial side of the brace for attaching a second end of the foot strap on the medial side of the brace, with the first and second ends of the foot strap being both located on the medial side.

20 Claims, 26 Drawing Sheets

Related U.S. Application Data continuation of application No. 16/619,239, filed as application No. PCT/US2018/036986 on Jun. 12, 2018, now abandoned.

(60) Provisional application No. 62/518,194, filed on Jun. 12, 2017.

(58) Field of Classification Search
CPC ........ A61F 5/04; A61F 5/058; A61F 5/05841; A61F 5/0585; A61F 5/05858; A63B 71/12; A63B 71/1225; A63B 2071/1258; A63B 2071/1266; A63B 2071/1275; A63B 2071/1283
See application file for complete search history.

(56)                   References Cited

U.S. PATENT DOCUMENTS

| | | | |
|---|---|---|---|
| 7,753,865 B1 | 7/2010 | Hely | |
| 11,617,672 B2 | 4/2023 | Ducharme et al. | |
| 11,826,273 B2 | 11/2023 | Ducharme et al. | |
| 11,974,935 B2 | 5/2024 | Amendola et al. | |
| 12,004,987 B2 * | 6/2024 | Ducharme | A61F 5/0127 |
| 12,036,141 B2 | 7/2024 | Ducharme et al. | |
| 2005/0133044 A1 * | 6/2005 | Goodrich | A61F 5/0111 128/882 |
| 2006/0030864 A1 | 2/2006 | Kennedy, II et al. | |
| 2010/0168631 A1 | 7/2010 | Scheffer et al. | |
| 2011/0196275 A1 | 8/2011 | Chang et al. | |

* cited by examiner medial side lateral side

1

LIVING HINGE FOR ATHLETIC BRACE OR SUPPORT

FIELD OF THE INVENTION

The invention relates to generally to an elastomeric athletic or orthopedic brace or support that includes a hinge system which includes one or more elastomeric supports members that is engineered to deform so as to allow and direct a preferential direction of movement through the support member. In particular, the hinge system forms a component in a brace having an external, adjustable network of elastomeric interlinking support bands that radiate out. The hinge is a "living hinge" meaning that it is an elastomeric hinge that supports the joint at its axis of movement, that it self-locales at that pivot point, and that is provides for an engineered movement of the joint as a result of its material and structural characteristics.

BACKGROUND OF THE INVENTION

The invention generally provides an athletic or orthopedic brace or support, which may include an elastomeric sleeve having fenestrations meaning in this instance, areas of reduced support, which may be openings or which may include an area of a softer or more yielding material characterized by a lower durometer material. More preferably, the hinge forms a component in a brace comprising an adjustable network of elastomeric interlinking support bands with or without an underlying web of material. In both cases, the brace surrounds and supports one or more joints so as to provide an external anatomically configured framework that mimics or augments the effects of the ligaments. In the environment of the brace, the invention includes a hinge system that is engineered to allow motion in a controlled manner, so that the supported joint may be flexed in a direction that is not harmful but where potentially harmful motion is inhibited by the brace.

Thus, the invention relates to one or more central support member(s) that defines an axis of motion. This support member is intermediate a first brace part on one side of the joint in question and a second brace part on the other side of the joint. The support member preferably comprises opposing hub members, such as on the medial and lateral side of the ankle, knee or elbow joint which members together define an axis about which a first member of the brace pivots relative to a second member of the brace. For most uses, the first brace part or top member can be a proximal member while the second brace part or bottom member can be a distal member, and for an exemplary embodiment for use on an ankle, the first brace part or top member is a leg member and the second brace part or bottom member is a foot member and the brace includes a medial support member or hub (i.e. a support which surrounds preferably at least 270 degrees, and advantageously, 360 degrees of the medial malleoli) and similarly, a lateral support member or hub. Together these hub members include an opening or weakened area in the middle which overlays the ankle bones (i.e. malleoli) to define an axis about which the ankle hinges and which the brace permits while still inhibiting movement in other planes, such as torsion or twisting.

Advantageously, the first and second brace members comprise a network of elastomeric supports, (preferably band members that are longer than they are wide and wider than they are thick so as to comfortably distribute the tension that they apply to the user) and also includes a plurality of strut members (once again elastomeric band members) comprising a first set of struts on the medial side of the ankle brace and a second set of struts on the lateral side of the ankle. The medial set of struts radiate outwardly from the medial support or hub and are linked to the periphery of the brace on the medial side and the lateral set of struts radial outwardly from the lateral support or hub and are linked to the periphery of the brace on the lateral side of the brace. The periphery comprises a cycle of reinforced portions which include a band (again having a geometry and dimension so as to optimally apply a tension to the user which is comfortable in use) which surrounds the proximal portion of the brace and one which surrounds the distal portion of the brace, and wherein the proximal band or anchor is linked to the distal band or anchor by an anterior band on the top of the brace and a posterior band or bands on the bottom of the brace. Advantageously the anterior band offset from the front of the ankle and the posterior or planar bans comprises a series of bands on the sole of the brace. The anterior band can include means for fastening or adjustment, including for example, the hook or loop of a Velcro fastening assembly. The mating portion of the fastening means can advantageously be held on straps that extend from the rear of the brace, such as a medial strap and a lateral strap which encircle the ankle and which spiral about the ankle so as to direct the tension of the brace around the ankle, and around the brace.

The spaced support members or hubs, pairs of radial struts and the peripheral linked support act to limit the lateral motion (i.e., side to side or torque or twisting) while allowing the hinging of the brace much in the way that the spokes of a wire spoked wheel or the cables of a tension bridge act to support the main body in tension while the main body member accepts and transmits compressive forces. In accordance with this invention, the support member or members are engineered to allow for preferential deformation of the shape of the support to preferentially allow or direct motion within or at the support member or members. More specifically, the support member includes a section of reduced rigidity, such as a section of reduced volume (including a reduced width, thickness or absent length i.e., a discontinuity such as a notch or gap) so as to encourage the deformation of the support at a specific location or for example, for a ringed band, a defined buckling or lapping which allows the first and second brace parts to hinge about an axis defined by the support member or hub. Alternatively, the section can be a section of material having increased elasticity, such as an area in which there is a lesser degree of cross-linking. Thus, the brace encourages motion, including rebound or re-coil in the permitted direction while inhibiting motion that is more likely to have the potential to harm the joint.

In the exemplary ankle brace, the medial or inside set of struts (i.e. elastomeric bands which act in tension as struts) thus includes one or two upwardly extending strut members that join at the bottom to the medial support or hub and on the top to a proximal harm of the brace network and one or two diagonally extending strut members that extend from the medial support or hub to a distal band of the brace network. The inside set of struts can also include a posterior set of struts that join to a rear band that encircles the heel of the user, or alternatively, the hub can connect directly to the rear band. Since the brace preferably is open at the heel and to the rear for entry, it includes a rear band that circles the heel cut-out and extends along each edge of the rear of the brace and joins to the proximal band. On one side, preferably the lateral side, the rear band extends into a strap, which laps over the medial side of the brace and fastens, such as about the top of the brace. The outside or lateral set of struts likewise include a corresponding network of radially extending, strut members (i.e., bands), such as one or two upwardly extending members that connect the lateral support or hub to the proximal edge and one or two diagonally extending strut members that connect the lateral support or hub to the front edge of the foot member and a downward strut that connects the lateral support or hub to the bottom of the heel band and a rearward extending strut that connects the hub to the rear portion of the rear band which extends into a strap that spiral from inferior to superior and across the front of the ankle to close the brace to a desired tightness. This configuration of the brace allows a rear entry brace which closes around the front in such a way that the closure means serve primarily for sizing and tightening, and are not subject to the direct forces that tend to cause closure means to wear out, for example, when the hook and loop of Velcro is tensioned along the direction of fastening.

Preferably, the brace further includes a sleeve or web of underlying elastomeric material which underlies the network of supports (i.e. framework of bands) so as to distribute the forces of the network over the users skin and to provide a comfortable layer which may include texturing, such as nibs, notches or perforations so as to increase the proprioceptive aspects of the brace and also to permit the brace to "breath" or to allow sweat to evaporate from under the brace. Likewise, the hinge aspect of the present invention can be used for braces for joints other than the ankle, including, the knee, ankle, or phalanges.

The hinge system of the invention can be used in braces which are used prophylactically (for example, allowing sufficient range of motion to allow the brace to be worn during athletic activities without hindering the athlete, but which acts to support the joint or joint complex and to inhibit potentially harmful motion) or the brace can be used therapeutically (for example, in the aid of healing of a joint or joint complex which has suffered some previous injury). The brace has application in all of the joints, including the shoulder, elbow, wrist, hand, thumb, foot, knee, hip and back and the concepts of the present invention can be applied to each of these joint complexes, but is illustrated specifically with respect to an ankle brace.

The present invention provides an answer to the issues of injury related and prophylactic joint support in the form of a hinged elastomeric brace that provides for directed and anatomically configured support, as well as proprioceptive reinforcement for the brace user. The brace of the present invention provides an increased PAR as compared to the prior art bracing which is a result of the support framework providing stop limited vector directed support in addition to or combination with surface achieved tactile response.

SUMMARY OF THE INVENTION

The brace is in the form of a hinge system which is a component of a brace that may be a sleeve (which can be considered a single unit that spans the joint or a first part on one side of the joint, and a second part on the second side of the joint) and formed from an elastic material in which a more distal portion comprises a loop, which is preferably a continuous loop, which encircles a portion on one side of the joint or joint complex and a more proximal portion that encircles the other side of the joint or joint complex. The brace further includes negative or void areas (i.e. "fenestrations"), such as weakened areas, recesses or apertures that act to re-direct forces through the complementary areas which assume the stresses in response to the existence of the negative area. In further embodiments the sleeve also includes or consists of (meaning there is no web in addition to the framework) a web or framework of stiffer, more rigid, or less elastic support members that interconnect with each other and between a proximal and distal anchor, each of which encircle the limb. This web or framework acts to augment the natural ligaments. In a way that provides support but which limits potentially harmful motion.

The ankle brace which illustrates the present invention includes the foot portion and the leg portion which join together at the ankle joint, and is comprised of an interrupted web (in this case meaning a flat, and potentially homogeneous cast or molded sheet) of elastomeric material in which the interruptions or openings together with the material characteristics of the elastomer define the manner in which the brace functions. In particular, the material forming the foot portion and the leg portion are separated by the heel opening and the TFT opening which allow the foot portion and the heel portion to form a joint there between, and to accommodate movement at the ankle joint without unnecessary material or bunching. This is a particular advantage for a soft brace that is worn underneath a shoe, other athletic footwear, or a shin guard. In addition, the combination of the malleoli openings and the two openings at the medial and lateral surfaces of the plantar covering of the foot portion of the brace act so as to provide direction as to resistance of force sustained within the web of material that is defined by the combination of the openings. Moreover, these openings are engineered to permit a relative pivotal motion between the foot, and leg parts, and this hinge system is formed by ringed support member (i.e., bands) that from a complete 360 degree circuit (optionally in some embodiments of the hinge member minus a small section such as 1-20 degrees, and preferably 2-10 degrees, and most preferably 3-7 degree), which may advantageously be a circle, oval, or ellipse, but which also form a linear support, such as a quadrangle, or a hexagon or geometric shape.

Thus, the brace of the current invention is designed to allow as much safe freedom of movement to the wearer as possible, but to provide resistance to movement that could be harmful. In particular, the device is intended to inhibit inversion in plantar flexion (and to help stabilize the syndesmotic ligament) so as to avoid "rolling" an ankle. The brace is intended to provide external support tantamount to external ligaments and or fascia, that reinforces in proper places but which relieves pressure where it is needed. Thus, the device acts in tension and compression to buttress the syndesmotic ligament at the top, and in the cross-configuration to buttress the ATFL (anterior tibiofibular ligament), and the CFL (calcaneal fibular ligament), with a medial web member that buttresses the deltoid ligament. In addition, the elastomeric nature of the brace material, and in particular of the hinge system, coupled with the form can act to provide energy re-balance to the wearer, where the kinetic energy is re-circulated or re-coiled to the user, while inhibiting potentially dangerous forces applied to the joint complex. The material also provides proprioceptive feed-back to the user and the elasticity and/or stickiness of the material helps to remind the user to maintain tone. It is preferable that the material is "alive" or slightly sticky to the skin of the wearer. A desirable level of stickiness would be the feel of slightly under-cured natural latex, or a material that has been exposed and allowed to dry to a solution of sugar-water, or something less adhesive than a traditional band-aid or a light masking tape. Acceptable values measured according to ASTM, D3330D/D3330M. Test Method F at 90 degrees, for peel adhesion of pressure sensitive tape, would be 0.0005-50 N/100 mm, preferable 0.5-30 N/100 mm, and most preferably 0.2-25 N/100 mm.

In a further embodiment of the invention, additional, and optionally external adjustable struts are provided to provide joint stability against typical directions of ligament strain. Specifically, as relates to the brace of the present invention in use for ankle support, the struts are provided as one or more additional add-on elastomeric strap members that extend diagonally across the lateral or medial aspect of the brace, and optionally including support over the malleoli to provide one or more line of support in two more or less orthogonal directions extending inferiorly to superiorly and posteriorly to anteriorly respectively and optionally running diagonally over the anterior surface of the ankle joint. In addition, depending on the indication, the supports can include footplates of wedged footplate to change the plantar plane of the foot. Since these straps can be added to the brace to supplement the brace itself, they can be provided with more or less stretch to provide for more or less support to the joint. Advantageously, the straps have easy attachment means, such as a the illustrated Velcro attachment or a puck and grommet mechanism, in which the straps include spaced apart pucks that can be pushed into a retained relationship with the grommet, and that can be popped out of engagement by pulling outward on the extensions. This aspect of the invention is illustrated in various embodiments in FIGS. 13-28.

In an adjustable version, the brace is in the form of a sleeve (which can be considered a single unit) that spans the joint or a first part on one side of the joint which comprises a flat web or band of material that is wrapped around a body on one side of the joint and is closed by closure means which provide for adjustability and for the ability to provide directed tensioning. The sleeve also includes a second part on the second side of the joint and formed from a continuous (i.e. integral) elastic material where a more distal portion comprises a loop, which is preferably a continuous loop (and here it is envisioned that this loop could also be formed by closing a flat web to form a circle), which encircles a portion on one side of the joint or joint complex and a more proximal portion that encircles the other side of the joint or joint complex.

The leg portion of the brace includes a proximal opening that encircles the lower leg sufficiently above the lateral and medial malleoli in order to provide a suitable proximal anchor on the leg of the user. A second distal anchor is joined at the foot opening. This portion of the brace also forms a continuous loop, but advantageously is openable, for example, to the rear, or preferably slightly lateral to the Achilles tendon, for entry into the brace, and also to provide adjustability in this portion of the brace. In a further embodiment, the first and second anchors are stiffer more rigid elements, formed for example, of a higher durometer material, (e.g. 85+/−30 and preferably 70+/−10, and most preferably 70+/−5 durometer on the Shore A scale.) The anchors are interconnected by supports or struts in the form of strips, or bands which have a much longer length than width more than 5×, and preferably more than 10× but where the width is between one-eighth to one-half inch and the lengths are from one-half to fifteen inches depending on whether the length is taken for a single segment, which may be as short as one-half inch or as long as ten inches extending along a line, or for an aggregate of a number of segments) of the same or similar material. The supports interconnect to form a framework or network of ligament complementary support which aids the joint and inhibits "harmful" motion while freely permitting acceptable motion. These supports can have a similar durometer as set forth above or one that is slightly lower (i.e. by 1-5 units on the shore A scale).

Various closure mechanisms can be used at the anchor juncture(s), including straps, bands, webs, and cables having a closure means that mates with a corresponding closure means on the lateral side of the sleeve. These closure means could include buttons, hooks, latches, ratchet mechanisms, post and pin, groove and slide, hook and loop, post and loop, Velcro, cables, and zippers to name a few. The present invention also provides novel mechanisms for closure of a soft and/or elastomeric brace.

The brace further includes negative or void areas, such as weakened areas), recesses or apertures that act to re-direct forces through the complementary areas which assume the stresses in response to the existence of the negative area. The weakened areas can comprise complimentary webs of softer, more yielding, lower durometer material, e.g. having a durometer of 35+/−10, and preferably 45+/−5, on the Shore A scale. This material may also include perforations, such as pores or holes of 0.0001-0.05 inch diameter, to allow for the evaporation of perspiration. These pores may also affect the softness of the material.

In further embodiments, the distal and proximal anchors are connected structurally by struts or supports which are different than the basic sleeve webbing (i.e., by bands, straps, laces, or cables which are less elastic than the remainder of the brace) so as to transmit forces directly between them and between the distal and proximal anchors by means of supports which can permit desired motion which is deemed to be within a healthy range of motion, but restrain undesired motion, which would be potentially harmful to a vulnerable joint. The higher stiffness (or lower elasticity or resistance to stretch) can be effected by a number of methods, including a change in material, a change in material characteristics, including cross-linking or durometer which can be caused by the manufacturing method or by the ingredients, or a change in the geometry, including thicker or wider or higher volume of material so as to direct, inhibit or manipulate forces transmitted to the affected joint during use. Preferably these supports extend radially from the malleoli supports much like a hub includes spokes in a spoke wheel, and the supports are linked to a peripheral support system which includes the proximal band, the rear band, the plantar supports, the distal band (which may include a v-feature to accommodate various foot widths and shapes) and an anterior support which may be offset from the medial plane in order to provide for a more comfortable fit.

Finally, the brace can include pockets for sensors including motion of pressure sensors, including for example, transducers or accelerometers, that can be used for kinetic assessment such as standard gait analysis, or athletic training. Alternatively, these sensors can be integrated or embedded into the brace.

Figure 1:
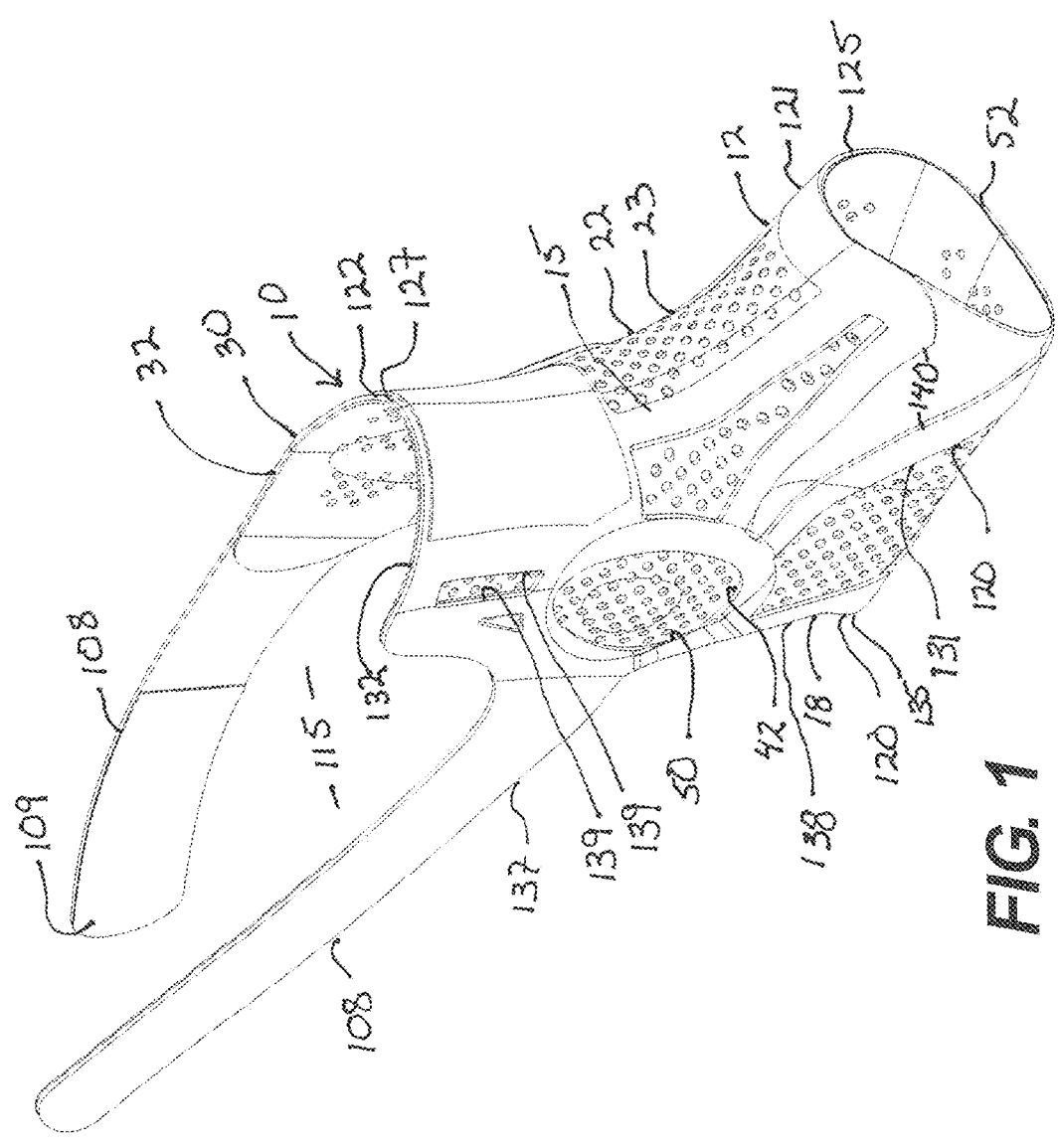
FIG. 1 is a front perspective view of the right ankle brace in accordance with the present invention shown on the ankle of a user.
Figure 2:
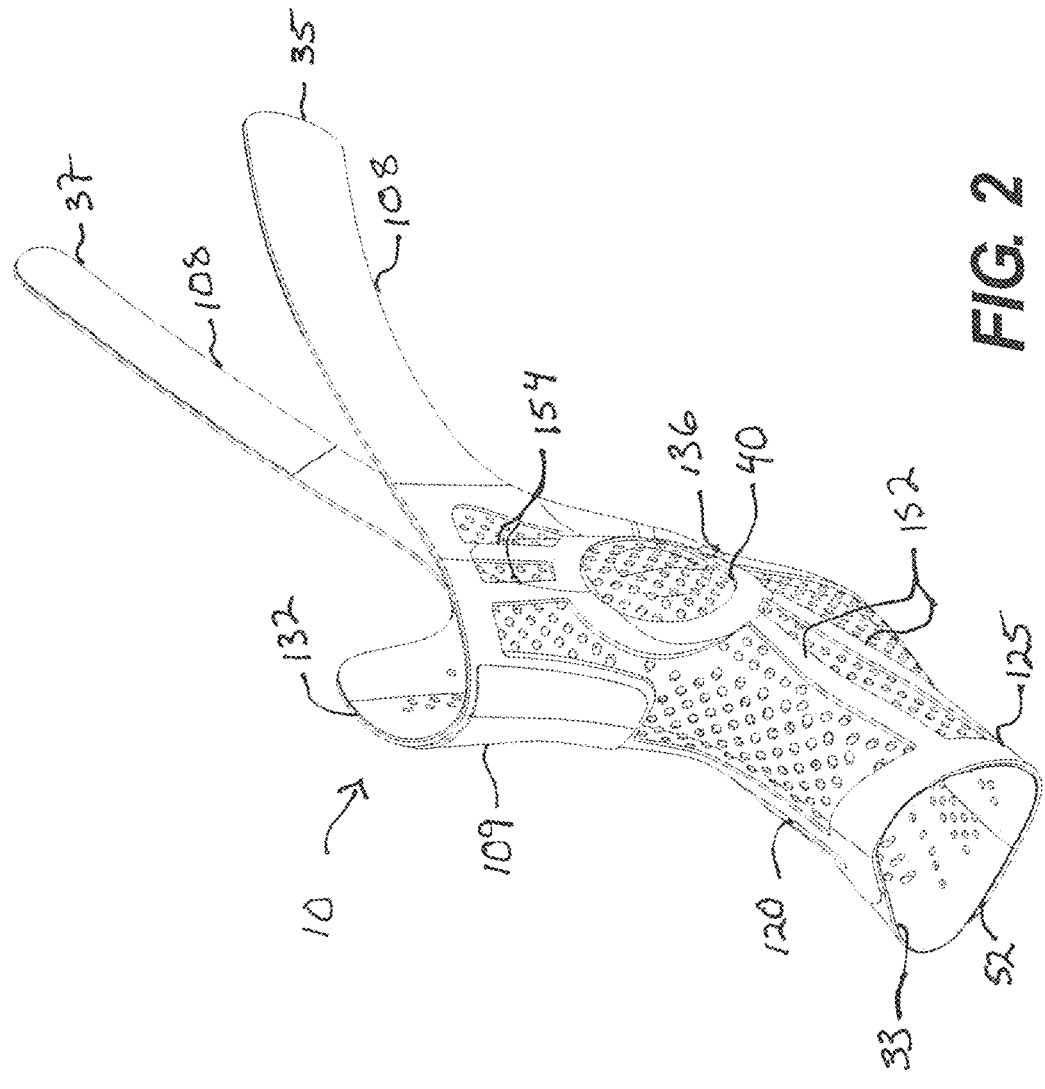
FIG. 2 is a top medial perspective view of the medial side of the ankle brace of FIG. 1.
Figure 3:
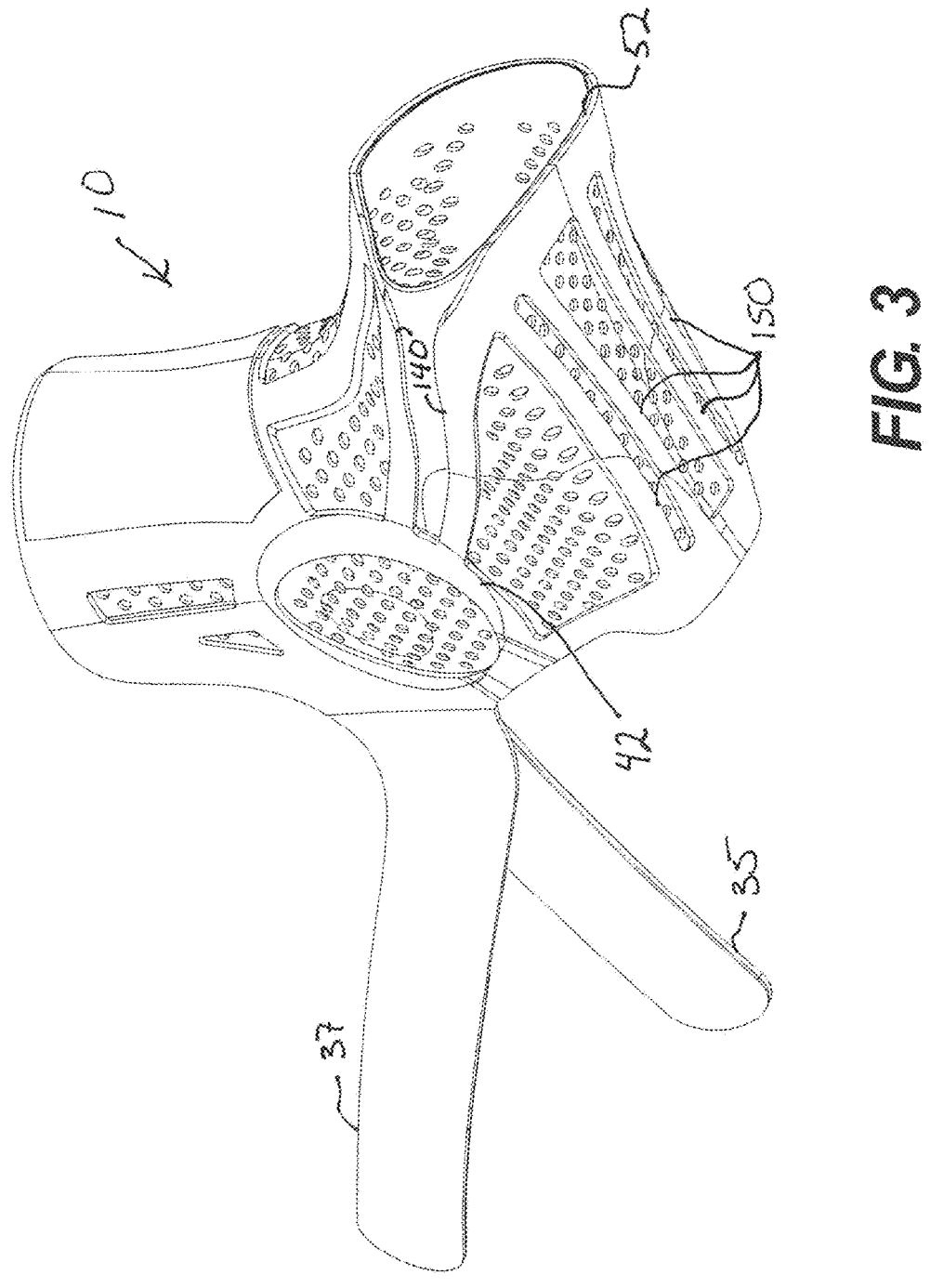
FIG. 3 is a top lateral perspective view the lateral side of the ankle brace of FIG. 1.
Figure 4:
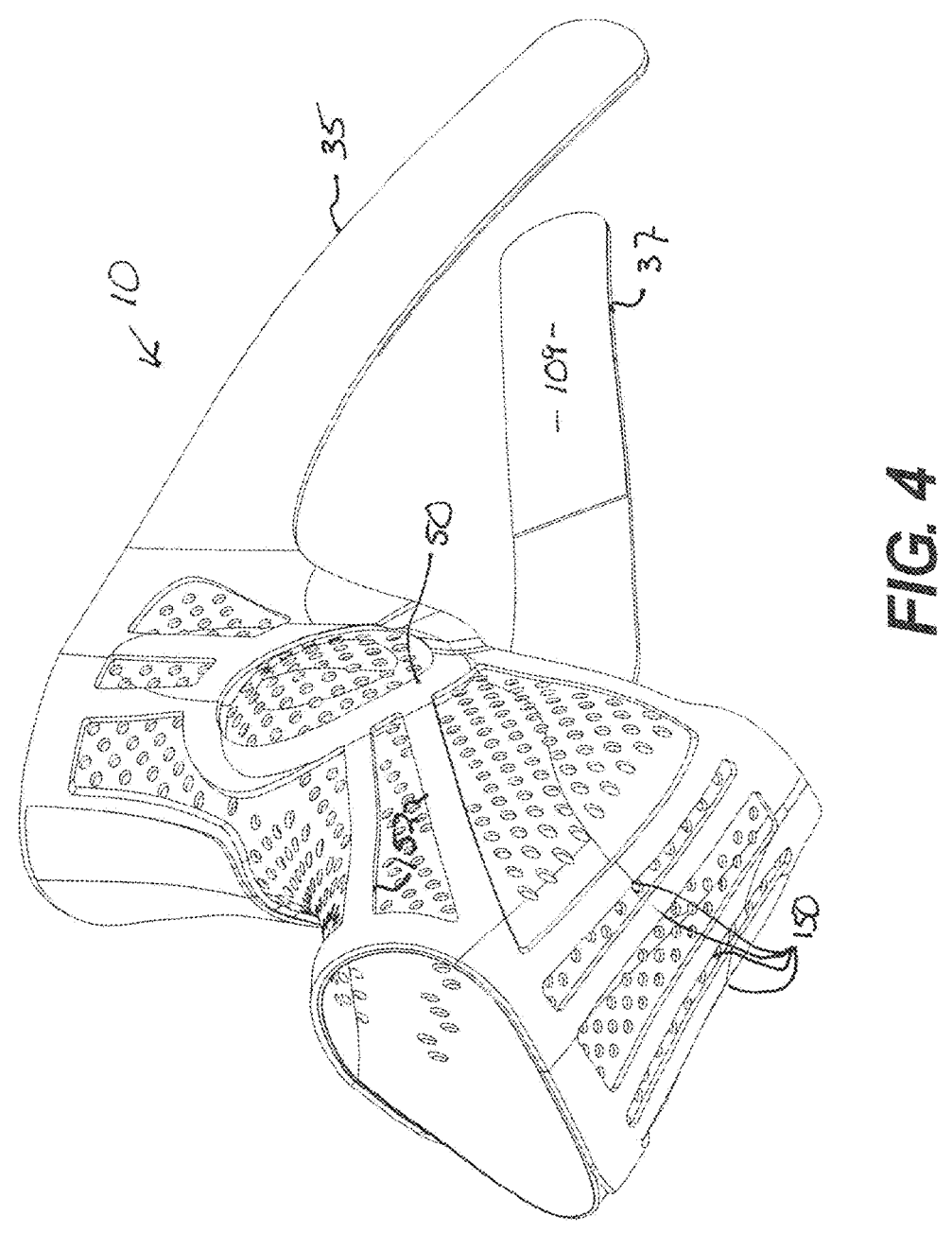
FIG. 4 is bottom medial perspective view of the ankle brace of FIG. 1.

DETAILED DESCRIPTION OF THE
INVENTION

The present invention is illustrated as a component of an ankle brace, but has been previously stated, could comprise a component of a brace for a different joint or even of a brace other than the illustrated brace. In the ankle brace 10 that is shown, a first part or more distal portion 12 encircles the mid-foot of the user 14 and a second part or more proximal portion 30 encircles the lower leg of the user. The brace is provided in a right version and a left version which are mirror images of each other, and also can be provided in multiple sizes, including for example small and large, or pediatric, ladies and men. The brace is illustrated as a right ankle brace and the left ankle brace is a mirror image of the right ankle brace shown.

The brace includes a web 22 of flat elastomeric compound or material, which, if opened, would form a flat sheet of relatively uniform or uniform thickness and comprised of a homogenous composition, which optionally includes reinforcing material such as fiber, but which is preferably not a mesh, woven or non-woven fabric in this configuration. The web can form a sleeve 23 comprising the web members of the foot portion 12 and the leg portion 30, and which underlays the interlinking network of relatively more rigid (i.e. compared to the sleeve material) bands of elastomeric support. The foot portion 12 has a distal opening 16 that is configured to snugly surround the user's foot, at approximately the neck of the fifth metatarsal through the plantar surface to the middle of the first metatarsal and arching proximally toward the tibial fibular talar joint over the dorsal surface of the foot. At the other end, the foot portion 12 ends on the plantar side posterior to the end of the medial arch in a heel opening 18 suitable to expose the fat pad of the heel (approximately one-half of the way posterior toward the heel end of the calcaneus) on the posterior side, and below the insertion of the gastrocnemius into the Achilles tendon as it extends upward on the leg to form the bottom boundary of the leg portion of the brace. The foot portion 12 ends on the anterior side of the ankle at the "eye of the ankle", i.e. on the superficial aspect of the anterior ankle at the joint of the tibia/fibula/talus (or the "TFT" joint). The foot portion 12 includes a web of material 22 (preferably molded or cast) that covers an area corresponding to the cuneiforms and the cuboid bone and the navicular bone. On the medial and lateral sides of the brace, the foot portion runs diagonally between the anterior and posterior openings where it joins the leg, portion 30 which surrounds the bottom portion of the leg or the vertical portion of the ankle approximately one-third of the way up the lower leg, and below the bellies of the distal aspect of the gastrocnemius.

The leg portion 30 of the brace includes a proximal opening 32 that encircles the lower leg sufficiently above the lateral and medial malleoli in order to provide a suitable anchor on the leg of the user for the forces applied by and to the brace. This portion of the brace also forms a continuous loop when it is closed.

In addition to the previously described openings including the two terminal openings there are several other functional negative areas or "fenestrations" (used herein to mean areas of decreased resistance, including for example through openings, as well as areas in which there are material changes, such as a more stretchy or less cross-linked or even a thinner web of material) in the brace. The two terminal openings include the first or distal most 16, having an edge that runs across the mid-foot on the plantar side, and arching back toward the TFT joint over the top of the foot to the proximal aspect of the metatarsals; and the second or proximal most opening 32 forming a roughly circular opening which encircles the lower leg about 1.5-3.5, and preferably 2-2.5 inches above the malleoli or a third of the way up the lower leg and below the belly of the gastrocnemius.

The functional openings include the opening at the heel 18, which is open to or excludes coverage of a significant portion (i.e. 75% or more or all of) of the surface area of the heel pad, having an edge just in front of the medial process of the calcaneal tuberosity, and on the leg portion of the brace just above the insertion of the Achilles Tendon superior to the calcaneal tuberosity. Further, the brace includes two openings that correspond 1) to the medial malleolus 40 and 2) to the lateral malleoli 42, in the present embodiment, on the medial side, the malleoli openings 40, 42 are roughly circular or oval in shape bounded by support bands which form a part of the hinge system as are further described below. These openings approximate a size slightly larger than an average size of a malleolus. The distal opening ends proximally in front of the tuberosity of the fifth metatarsal, and distally roughly 0.5-1 inch behind the terminal opening of the foot portion at the neck of the fifth metatarsal.

The brace includes the foot portion 12 and the leg portion 30 which seamlessly join together at the ankle joint to form one integrated surface, and is comprised of a web of elastomeric material having an interlinking network 15 of support bands or struts in which the combination of the web, the network of bands of external supports together with the material characteristics of the material define the manner in which the brace functions. In particular, the sleeves forming the foot portion 12 and the leg portion 30 are separated by the heel opening 18 and the network of support bands 15 include a pair of open malleoli supports 40, 42 including radially extending struts 44 which allow the foot portion and the heel portion to form a hinged joint 50 there between, and to accommodate movement at the ankle joint without unnecessary material or bunching. This is a particular advantage for a soft brace that is worn underneath a shoe, other athletic footwear, or a shin guard. In addition, the combination of the malleoli supports 40, 42 and the two openings at the medial and lateral surfaces formed between the medial and lateral support network and of the plantar covering 52 of the foot portion of the brace act so as to provide direction as to resistance of force sustained within the web of material that is defined by the combination of the openings. Further the malleoli supports include a mechanism to cause an engineered preferential deformation, which results in a hinging of the associated parts of the brace, Thus, the brace of the current invention is designed to allow as much safe freedom of movement to the wearer as possible, but to provide resistance to movement that could be harmful, in particular, the device is intended to inhibit inversion in plantar flexion (and to help stabilize the syndesmotic ligament) so as to avoid "rolling" an ankle. The brace is intended to provide external support tantamount to external ligaments and or fascia, that reinforces in proper places but which relieves pressure where it is needed. Thus, the device acts in tension and compression, to buttress the syndesmotic ligament at the top, and in the cross-configuration to buttress the ATFL (anterior tibiofibular ligament), and the CFL (calcaneal fibular ligament), with a medial web member that buttresses the deltoid ligament. In addition, the elastomeric nature of the brace material, coupled with the form can act to provide energy re-balance to the wearer, where the kinetic energy created in a muscular exertion of the user is re-circulated or re-coiled to the user, while inhibiting potentially dangerous forces applied to the joint complex. The "spring" that results, and the resilient contact of the brace with the surface of the ankle, also provides a proprioceptive feel to the user that helps to protect the ankle joint.

It is a further advantage in some instances to provide the brace with supplemental support means that can be adjusted to suit a particular user. This embodiment is also illustrates a rear opening aspect of the invention in which the leg portion has an opening 115 between the medial and lateral portions that preferably overlap or abut each other to encircle the leg, and from which straps 108 extends to allow for closing, tightening or tensioning, and which also include closure means, in this illustrations hook and loop or Velcro fastening means 109. It is of advantage that the support means act to inhibit stress to the syndesmotic ligament, to the TFTL, and to the TCL. Thus, the support means advantageously extend from the plantar supports covering (or optional footplate) diagonally upward across the anterior hinge of the ankle in the vicinity of the cuboid and navicular bones, and possibly even to a further support member or anchor at the proximal end of the lower leg portion of the brace. These means can include straps, laces or cable members that are designed so as to provide for adjustable degrees of tensioning, as well as adjustable directions of tensioning to allow the wearer to customize the feel and size. The device acts in tension and compression to buttress the syndesmotic ligament at the top, and in the cross configuration to buttress the ATFL (anterior tibiofibular ligament), and the CFL (calcaneal fibular ligament), with a medial web member that buttresses the deltoid ligament.

The present invention is designed to provide some syndesmosis stability above the malleoli. In a further adjustable embodiment, it illustrated with a rear entry, i.e. open toward the posterior portion of the leg, but with an adjustable closure fixation point more anterior or anterolateral, (preferably not medial), with tension from posteromedial to lateral so as to pull the fibula anteriorly to help with syndesmosis stability and ankle. The optional superior band, is comprised of a reasonably high tensile strength to protect the syndesmosis. The brace is designed to provide a definite end to plantar flexion and inversion and also some level of protection on the syndesmosis.

It is envisioned that the brace comprises an interlinking network of supports 120 or elastomeric bands such as struts built into the lateral and medial side of the brace on the lateral side of the brace radiating outward from the medial 40 and lateral 42 malleolus supports and extending between the foot portion 12 and the superior portion of the leg support 30. On each of the lateral side and the medial side the supports or struts 120 form a first portion 121 to support the foot and a second portion 122 to support the leg of the user. The first portion and the second portion are hinged at the ankle joint at an axis of rotation that permits the ankle to hinge about the line 50. This hinge is formed by the provision of a medial hub at the medal malleolus support 40 and the lateral malleolus support 42. The first portion is joined to a distal band 125 that encircles the foot and a proximal band 127 that encircles the leg. The network is connected to these anchors, which act to support the struts in tension and to allow the interlinking network 10 actually support the ankle in movement, like the spokes of a wire spoke wheel or a cable bridge. The struts comprise a series of struts which include one a lower lateral strut 131 connecting the malleolus support 42 to the band 133 and a lateral posterior strut 135 connecting the lateral malleolus support 42 to the extension of the heel band 133 defining the heel opening which in this case forms a closure strap 137. The struts also include two superior lateral struts 139 which connect the lateral malleolus support 42 to the top band 132 which form the top anchor for the leg portion of the brace. In addition, there are two anterior struts 138 which connect the lateral malleolus support 42 to the distal foot band that forms the foot anchor 134. Preferably, these two anterior struts form a gusset 140 or v-shaped link to the foot band 134, which is disconnected between them distally so as to allow the foot band to have a degree of give to accommodate various foot shapes and to allow the brace to be put on.

On the medial side, there is a corresponding first foot portion of interlinking bands and a second leg portion of interlinking bands or struts which connect the medial malleolus support (i.e. a ring which is circular or preferably oval to encourage hinging that surrounds the malleolus). The medial struts include a pair of anterior supports 152 that join the malleolus support 42 to the foot anchor 125 and a pair of superior struts 154 that join the malleolus support 42 to the proximal band 12 which forms the leg anchor for the interlinking network of bands. At the rearward portion of the interlinking network, the medial struts join directly into the medial heel band member 136, which joins with the proximal anchor and extends into the medial strap which closes the brace at the top of the brace. The lateral strap and the medial strap include closure means 109, such as hook and loop that join with a mating closure means 109 on the leg portion of the brace. The brace is designed so that the hook and loop avoid tension in the line of fastening. Thus, the hook and loop can be used to size and tension the brace, but resist the problems often encountered with this type of fastening means, such as loosening, opening or wear.

These struts 120 should have a definite endpoint at say 90-110% of physiological plantar flexion/inversion before easing to a firm stop at which point there is recoil. The struts are band members which are from 2-10× (and preferably from 3-8×, and most preferably from 4-6×) as wide as they are thick. The basic sleeve of the brace is intended to be very tight on the user with a low tensile strength and durometer so that it molds well to the ankle. The struts have a high tensile strength that cases to a firm end-point before recoiling. This is advantageously accomplished by providing elements (for example such as one or more fibers, cable or bands that are optionally sinusoidally placed) that have a high resistance to stretch embedded within or carried on the elastomeric sleeve member. This brace acts in tension rather as a buttress as in the prior art.

In addition, tensioning or closure mechanisms permit the wearer to pull through them and get a feel of tension, which provides a reassuring feel to the wearer. This tension is set such that it could result in a very high tensile strength at the end of range of range so that it can be really quite stiff within a range that is totally safe for the user. Optional closure mechanisms include various mechanisms, such as Velcro, watch strap level backs closure, hook and eye, pin and post, buttons, zippers, cables, laces to name a few. One advantageous closure is a watch strap type closure with a pulley at sinus tarsi level to retain the tensioning bands in an anatomical position, and having tensioning posts protected with a hinged door on a button at the fibula for extra security. Also, the tensioning mechanism can include a winding mechanism that translates the rotation of a tensioning dial member to the tensioning strap in order to increase the tension provided by the tensioning strap.

The leg portion 30 of the brace includes a proximal opening 32 that encircles the lower leg sufficiently above the lateral and medial malleoli in order to provide a suitable anchor on the leg of the user. This portion of the brace is open to from a planar web 33 (i.e, a flat band) that can be closed to form a continuous loop about the lower leg. The web 33 includes one or more extension 35 that can be a strap or band of varying thickness and which is of a length preferably so that the leg portion 30 fully encircles the lower leg and that the strap, band or cable 35 that extends from a first side of the web 33 can be pulled to a desired tension and secured by means of closure means 109 on the strap or medial side to mating closure means on the lateral side of the web 33. The embodiment shown includes an upper strap 35 on the medial side and a lower strap 37 on the lateral side which spirals upward about the leg portion of the brace. Various closure mechanisms can be used at this juncture, including straps, bands, webs, and cables having a closure means, that mate with a corresponding closure means on the lateral side of the sleeve.

The superior band 35 is integral with the top (i.e., the superior edge) of the leg portion 30 of the brace and at least in part, defines the size and shape of the proximal opening 32 that encircles the lower leg. The superior band 35 includes a closure mechanism that mates with a member on the band or on the brace body or on an attachment or strap on the brace to allow the closure of the brace, as well as sizing and tensioning as is desirable. The brace also includes a posterior band 37 which closes the rear of the leg portion 30 closer to the ground and which can overlap from the medial to lateral side as shown or from the lateral to medial side. The posterior band 37 also includes a closure mechanism, which cooperates with a mating member on the brace.

The brace is shown with a series of plantar supports 150, which connect the heel band and the distal foot band that forms the front anchor. Alternatively, these supports may instead be comprised of a plantar foot plate which may be thicker on one side than the other to change the angle of the foot.

Preferably when closed the rear opening of the brace 115 starts at 6:00 o'clock and extends laterally. This avoids the overlap occurring directly posterior to the Achilles tendon, which could cause aggravation with running, jumping or use of the ankle joint over time. The medial flap of the leg portion is pulled counterclockwise toward the lateral flap which tends to thin the material our slightly (depending on the Poisson's ratio) and resulting in less thickness and a lower profile. Optimally the overlap in the sulcus with the lateral flap is at about 4:30-5:00 o'clock (relative to the anterior medial line). The lateral flap is thinned down near the slit to 1.5-2+/−0.5 mm in thickness. The strap and material are designed so that a short distance pull creates a relatively large amount of stress. The placement of the mating lateral closure members is thus dictated on the configuration and material choices so that multiple locations close together results in a wide selection of resulting tensions and sizes, and allowing the user a significant range of tension within a small range of pull.

The pulling takes the posterior flap to 5:00 o'clock post tensioning. This allows about 90 degrees of workable circumference for placement of the lateral closure means. Preferably, the closure means are low profile and will not aggravate the user. The bands coming off the medial flap can be relatively short and thus result in good tensioning reproducibility and also for a significant amount of tensioning with a relatively stiff elastomer. Preferably the bands originate from a hard polymer, which is embedded into the end of the sleeve to provide increased durability and a more even pull. The bands can taper in height, taller at the origin, and thinner at the insertion (i.e. the location of the male closure) to further distribute the stress. There is optionally a pull connected to the male closure member, such as a stiff polymer or cloth which acts as a handle for the user during assembly and which will lay flat when the closure means is assembled.

Also the brace may be provided as an adjustable brace with a rear entry and closure means that allow sizing of the open portion. For example, it is advantageous to provide an open loop for the leg portion which can be tailored to a desired size, and which can even be re tailored at a later point. The anatomic location of the closure mechanism is important, and ideally, this is at the posterolateral aspect of the ankle joint; housed between the Achilles and distal fibula. This minimizes the interference with many athletes' function as well as minimizes general interference incurred during gait, again, depending on the mechanism of choice. Alternatively, the closure mechanism can be located on the medial side with the tensioning means (or straps) pulling in the direction of the struts laterally. Advantageously, the tensioning means provides for one-half to 1 centimeters of adjustability, (in particular if the brace is provided in three sizes), depending on the material of the tensioning means and the size range for which the brace is intended.

In addition, in a further embodiment, the brace is illustrated as including a framework of a stiffer (i.e. higher durometer material of approximately 75 durometer+/−15, preferably +/−10 and most preferably +/−5 on the Shore A scale. This framework 300 includes a proximal anchor, which encircles the upper leg and in this case includes a strap which engages a closure mechanism on the front of the brace. The proximal anchor is a band and forms a flat continuous (i.e. looping back on itself) ring 35 of relatively narrow width and constant thickness and which circles the foot. Advantageously, the ring also includes at least one, but optionally more, (i.e. two three, four or more), v-shaped (or other shape which include a wider opening and a tapering portion which resists but will allow for expansion of the circumference of the ring) gusset which allows the proximal anchor to expand without losing its function as an anchor in order to allow for size variations of the wearer. The framework also includes an opening 42, 40 on each of the lateral and the medial sides, preferably oval as previously described, to accommodate the malleoli. Struts extend from the proximal anchor to the malleoli openings. Further struts extend upward from the malleoli openings to the proximal anchor to complete the circuit between the distal anchor and the proximal anchor. This brace also includes a lower strap 37, which wraps the ankle at a lower position and from the lateral to the medial side and fasten at a hook and loop (i.e. Velcro) on the front of the brace 109. This area is stiffer and helps to support the anterior portion of the brace framework. The framework front support forms a base for the leg portion of the closure mechanism, and a rear member 136 frames the heel opening and is linked to the rest of the brace through links to the malleoli openings. The fenestrations in this case, are actually areas of integrated softer material, for example having a durometer of 40+/−10, and preferably +/−5 on the Shore A scale. This material is a relatively soft sheet of elastomeric material, with a uniform thickness from surface to surface, which is slightly sticky to the touch, as can be formed by injection molding or by casting at a lower cross-linking. This softer portion of the sleeve can also include perforations to allow for perspiration, or can include texturing to the surface for proprioceptive reasons. The web portion at the gusset may be advantageously strengthened, for example by eliminating the perforations in the remainder of the web in order to provide for greater strength here since the front of the network is open from the network to provide for greater fit.

The brace is made, for example by molding such as injection or transfer molding, liquid silicone molding or reaction in mold casting, a bio-compatible elastomer from a material of suitable durometer to provide the desired fit, and elastomeric characteristics. The brace preferably is made of a material that exhibits equal stretch in at least two dimensions (i.e. the X, Y directions). This material can be made more resistant to provide further support, for example of the syndesmotic ligament, by various means, including the additional of supports or struts which might be provided by an integral (same material) thickening of the brace in a defined area, or by changes in the material itself, such as higher rate of cure or cross-linking or the addition of other materials such as reinforcing fibers or the use of a second elastomeric material having greater resistance to an applied force, like a higher durometer or Young's modulus or modulus of elasticity, and which could be embedded in the brace, co-molded, or adhered to the inside or outside of the brace. The brace is designed to allow motion with a limited end-point; to encourage the recoil of energy and to allow for the potential prevention of harmful forces, i.e. the brace permits motion that is safe within a defined range, but inhibits abnormal or dangerous motion.

The brace forms a two part sleeve which is in substantial contact with the skin of the user between the two terminal ends of the brace. Thus, in the first embodiments, while there are fenestrations or openings in the brace, the remaining web occupies at least 40%, and preferably at least 50%, and even more preferably at least 60% or 75% of the area defined by the outline of the brace. In the embodiments having a more rigid framework and fenestrations with a softer web of material these ratios are reversed. The inferior surface may advantageously include a mesh, surface treatment or textured finish to increase the breathability and to prevent slippage.

In addition, the material is intended for a particular tactile experience at the surface of the skin of the wearer so as to provide a proprioceptive reminder to the wearer of the type that has been found to help inhibit ankle sprains. It is preferable that the brace has a slightly tacky feel at the skin interface. Thus, the brace provides bio-feedback to alert the stabilized joint so that it acts to inhibit undesired motion within that joint. In further embodiments, the brace may be put on wet, or over an inner sleeve that helps to enhance the tactile experience, such as including a roughly textured surface having a pattern of bumps, ridges, dimples, cross-hatching or protrusions.

The brace of the present invention can be used in a variety of joints. While the present invention can be used for hinged joints it is preferably for use in joint complexes, so that for example the "ankle" brace actually is intended to stabilize the ankle, subtalar and talonavicular joints, and the concepts set forth herein can be useful in support of other joints, including for example those located at the wrist, the elbow, the shoulder, the knee, and the fingers.

The present invention also has application for treatment of plantar fasciitis, medial and lateral (elbow) epicondylitis, toe and finger/thumb synovitis. A particular advantage of the present invention is that the brace is designed to "stretch" to a defined endpoint and that an effective "stop" is reached by a tension in member that acts like an elastomeric "ligament" placement. This can be provided by a change in structure of the brace, such as increased volume of material designed to limit the stretch, a different material characteristics, such as a higher degree of cross-linking, or change in material including for example, a cohered portion along a lateral edge, or an adhered portion along a top or bottom surface (including fabric which could be woven, and which could serve additional purposes, such as skin interface, bacterial or fungal control or odor control), or embedded materials, such as fibers or wires which exhibit relatively little stretch and are configured to provide a limit to a range of stretch at a given stop point.

The invention relates generally to a molded elastomeric sleeve of a biocompatible material having a defined hardness and elasticity, shape and configuration in three dimensions (adapted to the anatomy of a hypothetical user). For the ankle this means a brace configured to end on the foot at the neck of the fifth metatarsal and on the lower leg below the belly of the gastrocnemius, and having an opening at the heel cup and at the eye of the ankle joint, at the medial and lateral malleoli, and at the navicular bone and optionally including additional support of additional material or a stronger or less elastomeric material on the lateral side which resists a force applied to the ankle in inversion, including, for example, an integral support or attachment such as a tension strap positioned anterolaterally to simulate the reaction of the ATFL for more anterolateral stability where there is a support for syndesmotic stability, and one for ankle stability.

The basic sleeve of the brace is intended to be very tight on the user with a low tensile strength and durometer so that it molds well to the ankle. The material of the brace is ideally an elastomer, including for example, a thermoplastic elastomer having a Shore A hardness of 2-50 at 10 sec when measured in accordance with ASTM D2240, and a tensile break at stretch of 2-6 MPa at 23 degrees Celsius using Die C2 hour when measured in accordance with ASTM D412, a tensile stress of 0.08 to 0.8 MPa at strain 100% and 0.2 to 1.5 MPa at 300% at 23 degrees Celsius using Die C2 hour when measured in accordance with ASTM D412, and an Elongation at break of 800-1200% at 23 degrees Celsius using Die C2 hour when measured in accordance with ASTM D414, a tear strength of 7.5-20 kN/m when measured in accordance with ASTM D624, and a compression set of 5-30% at 23 degrees Celsius and at Time 79200 sec when measured in accordance with ASTM D395. Thermoplastic elastomers are suitable materials, with material sold under the trademarks Versaflex CL30, and CL2000X from Poly-One being preferable materials, alone, or compounded with additional materials, such as other cross-linking agents, additional elastomers to achieve material characteristics, reinforcing fibers and fillers, antimicrobial agents, colorants, and fragrances.

The brace in accordance with the invention includes struts laminated or adhered to the outer or inner surface or embedded within the sleeve member, and which have a high tensile strength that eases to a firm end-point before recoiling. This is advantageously accomplished by providing elements (for example such as one or more fibers, cables or bands that are optionally sinusoidally placed) that have a high resistance to stretch embedded within or carried on the elastomeric sleeve member. This brace acts in tension rather as a buttress as in the prior art. The brace could further include a fabric backing over an entire surface or over portions of surface in order to control the directions of resistance including a weave such as a bias weave fabric, which limits the stretch to one axis and inhibits the stretch along the other two axes.

The through thickness of the sleeve will depend on the material and elasticity but is preferably "low profile" meaning that it can be worn, optionally with socks, under a user's pre-owned shoe, meaning that it does not require a different size than is worn without the brace. Preferably the thickness would be form 2-to-10 mm, with about 5-8 mm on the lateral side and such that the brace still fits into the shoe and is cutout to go around the bony eminences. The medial side does not require the same resistance and could be 3-4 mm.

As designed, the brace optionally includes a self-formed (meaning that the foot plate is only loosely defined by an area of increased thickness or hardness, and that the wearer's foot acts to define the shape of the footplate in use) foot plate which contours around the heel more distally around the base of the fifth, so as to improve ST (sustentaculum/talar) joint stability. Alternatively, the footplate could be integral with the remainder of the brace, but could be more definitely defined, for example, by formation of a different, and potentially stiffer, or harder material. Thus, the foot plate could optionally be provided in a different material, for example a harder, or less stretchy material or this could be accomplished using a different configuration. Also, the footplate could optionally be thicker by 0.5-2 mm on the lateral side for approximately the length of the foot plate or at least 50% of the length and approximately one-fifth to one-third of the width to bias the foot to the outside and in order to promote control the tension on the syndesmotic ligament.

The brace is intended to last at least one season of intermediate level of non-professional use (i.e. 2-3 times per week), which is based on usage on the idea that the running shoes need to be changed every 300 or so miles, which is approximately 7-8 miles per week in a 9 month soccer season, or alternatively for one month of heavy use, and wherein the limiting factors include the continued support and configuration integrity, odor-free characteristics, and stickiness or tack to provide for the proprioceptive reinforcement.

The invention relates to an ankle brace for a hypothetical user having a leg including an ankle joint complex extending from below a gastrocnemius at the proximal side to behind the neck of a fifth metatarsal on the distal side, the brace comprising a sleeve formed from a sheet of biocompatible elastomeric material having a through thickness of from 1 to 7 mm, and the brace has a first portion which is a web formed from the sheet of the biocompatible elastomeric material which forms a first continuous loop about a first axis and a second portion which is a web formed from the sheet of the biocompatible elastomeric material that forms a second continuous loop about a second axis; and the first portion of the web having a proximal end which includes a top opening sized to fit below the belly of the gastrocnemius of the hypothetical user and the distal end of the first portion being connected to the proximal end of the second portion at a conjunction of the first portion and the second portion, and the distal portion of the second portion including a bottom opening sized to fit posterior to the neck of the fifth metatarsal of the hypothetical user; and the web including at least a first fenestration at the conjunction of the first and the second portions which is configured such that the first axis and the second axis are not the same.

It also relates to the previously described ankle brace as set forth above wherein the fenestration is a through hole and wherein the fenestration is an area of decreased resistance in the web and wherein the first portion of the web includes at least one opening for the lateral malleolus and wherein the first portion of the web includes at least one opening for the medial malleolus.

The invention relates to the previously described ankle brace wherein the elastomeric material is a thermoplastic elastomer having a Shore A hardness of 5-95 at 10 sec when measured in accordance with ASTM D2240 or a tensile break at stretch of 2-6 MPa at 23 degrees Celsius using Die C2 hour when measured in accordance with ASTM D412 or a tensile stress of 0.08 to 0.8 MPa at strain 100% and 0.2 to 1.5 MPa at 300% at 23 degrees Celsius using Die C2 hour when measured in accordance with ASTM D412 or an Elongation at break of 800-1200% at 23 degrees Celsius using Die C2 hour when measured in accordance with ASTM D414 or a tear strength of 7.5-20 KN/m when measured in accordance with ASTM D624 or a compression set of 5-30% at 23 degrees Celsius and at Time 79200 sec when measured in accordance with ASTM D395 where the elastomeric material could be a elastomeric material is a thermoplastic elastomer sold under the trademarks Versaflex CL30, and CL2000X from PolyOne including such an elastomeric material compounded with an additional materials selected from the group comprising other elastomers, cross-linking agents, reinforcing fibers and fillers, antimicrobial agents, colorants, and fragrances, and in particular wherein the reinforcing fiber is selected from glass, steel and carbon fiber. And this ankle brace could be formed by molding or casting.

The ankle brace also relates to an ankle brace for a hypothetical user having a leg including an ankle joint complex below a gastrocnemius at the proximal side and behind the neck of a fifth metatarsal on the distal side, the brace comprising a sleeve formed of a web of biocompatible elastomeric material having a through thickness of from 1 to 7 mm, and a that has a first portion which forms a first continuous loop about a first axis and a second portion that forms a second continuous loop about a second axis; and the first portion of the web having a proximal end which includes a top opening sized to fit below the belly of the gastrocnemius of the hypothetical user and the distal end of the first portion being connected to the proximal end of the second portion at a conjunction of the first portion and the second portion, and the distal portion of the second portion including a bottom opening sized to fit posterior to the neck of the fifth metatarsal of the hypothetical user; and the web including at least a first fenestration at the conjunction of the first and the second portions and the ankle brace further comprising a removable support member which provides resistance to a force applied to the anterior tibiofibular ligament.

Figure 5:
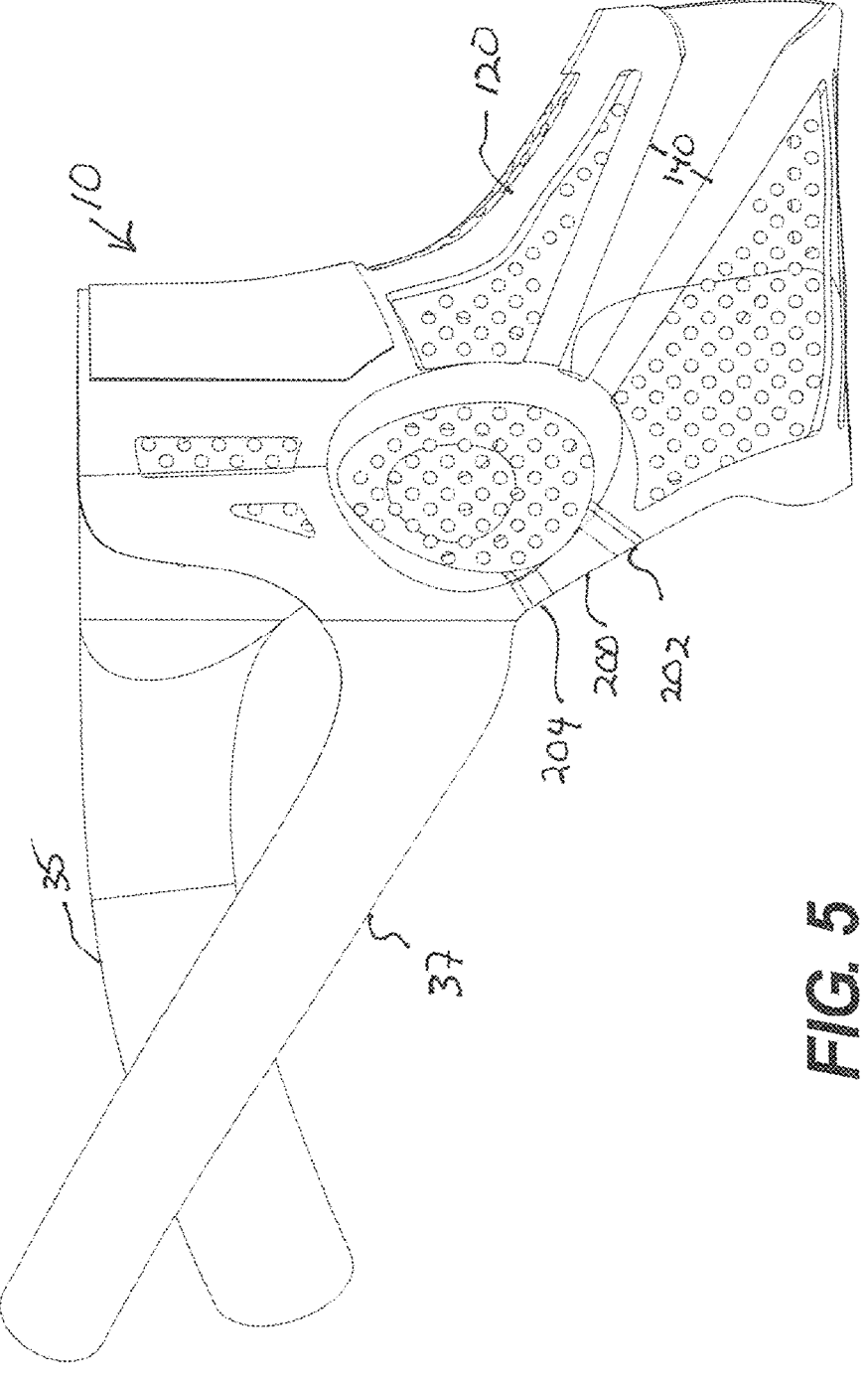
FIG. 5 is medial side view of the brace of FIG. 1.
Figure 6:
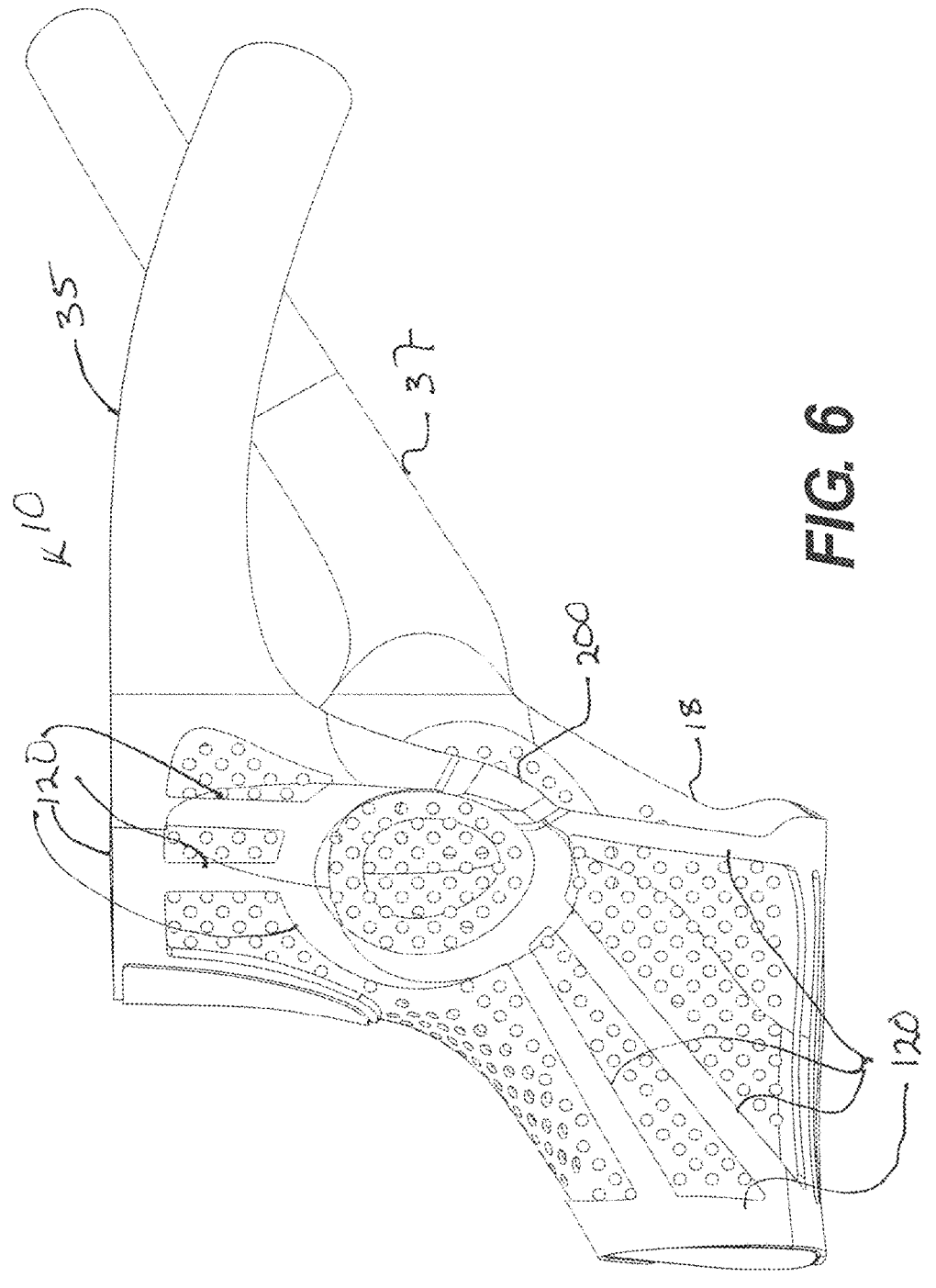
FIG. 6 is a lateral side view of the brace of FIG. 1.
Figure 7:
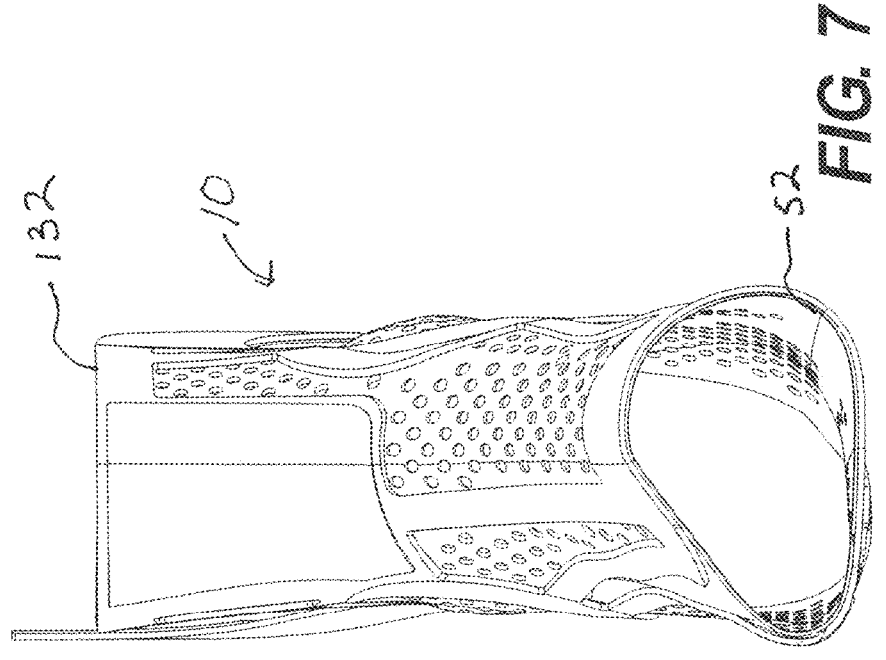
FIG. 7 is a front view of the ankle brace of FIG. 1.
Figure 8:
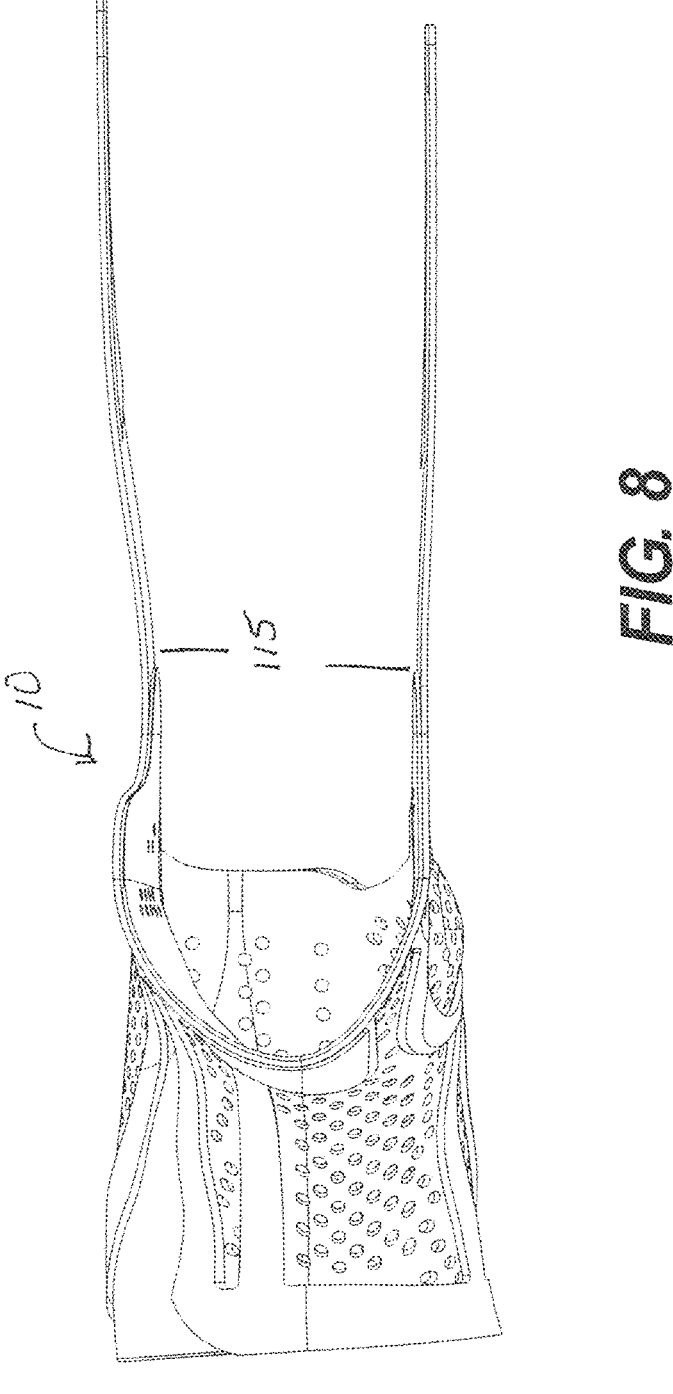
FIG. 8 is a top view of the ankle brace of FIG. 1.
Figure 9:
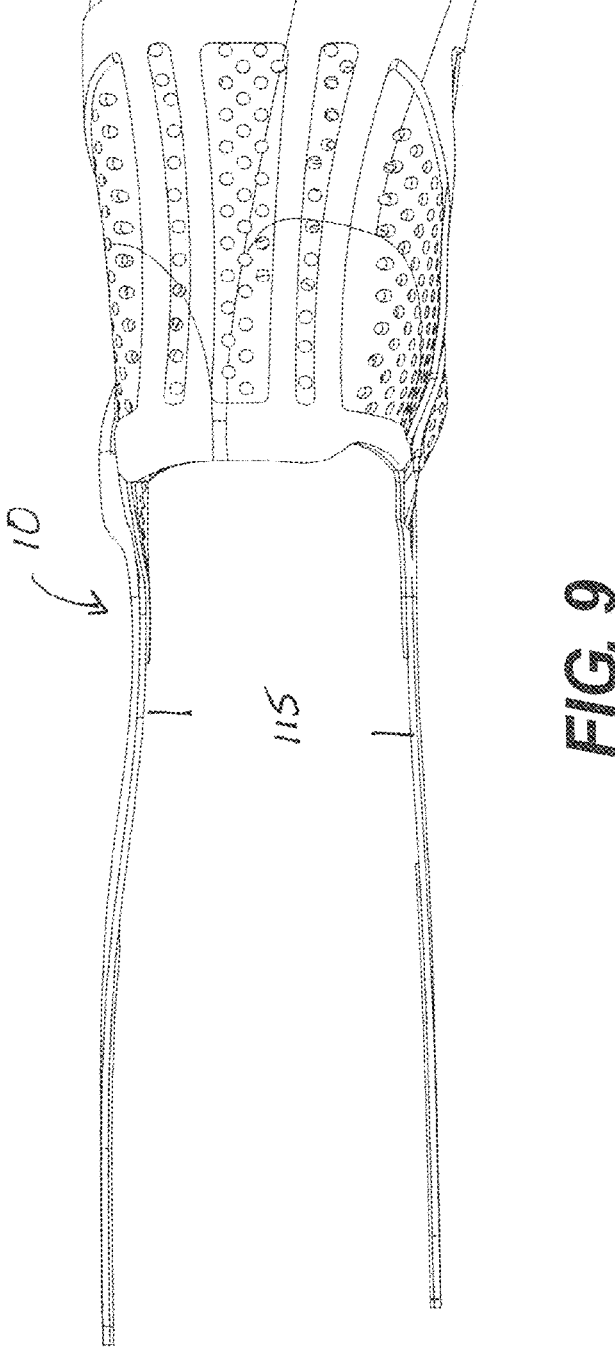
FIG. 9 is a bottom view of the brace of FIG. 1.
Figures 10, 11, 12:
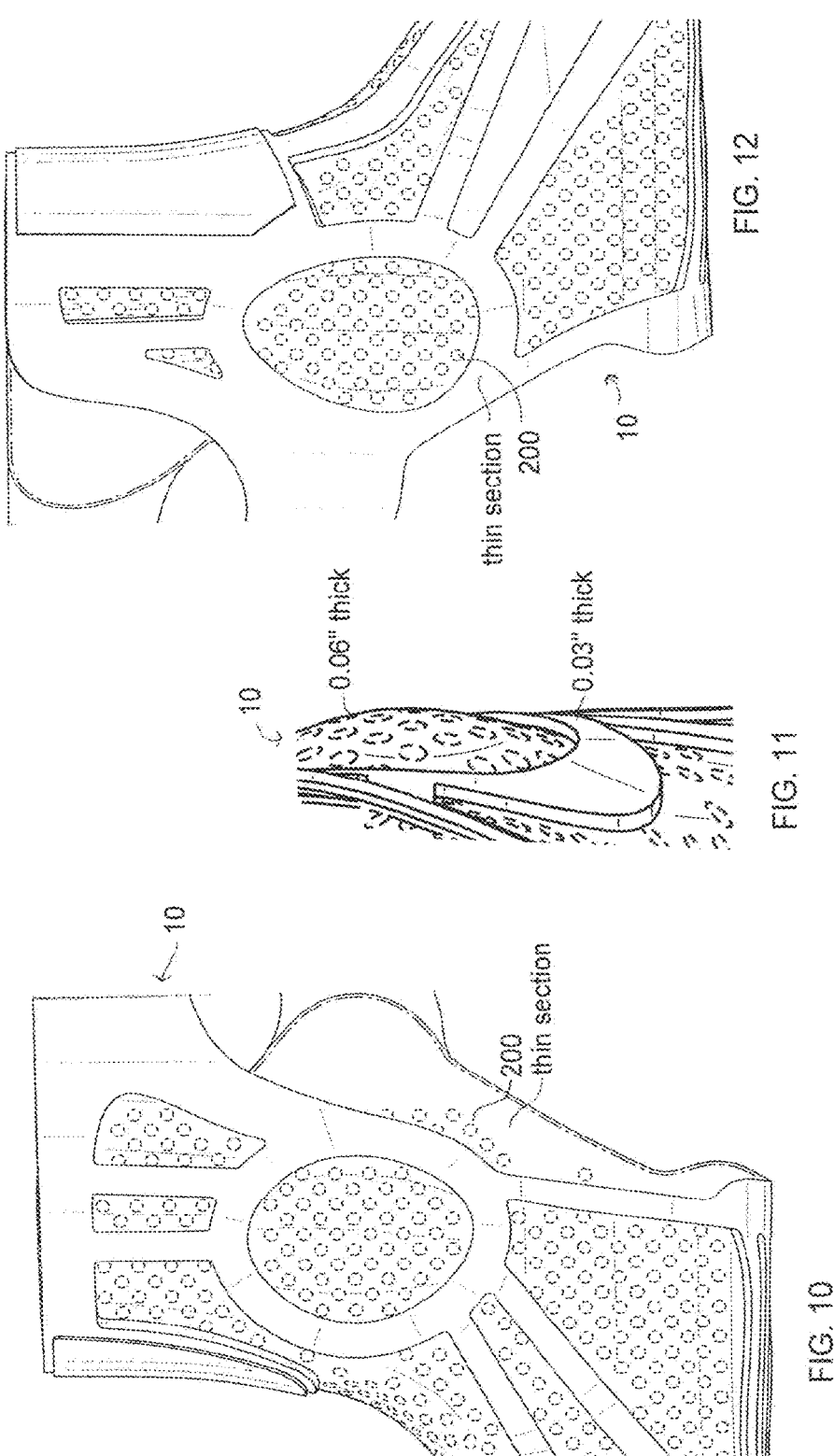
FIG. 10 is a detail of the lateral side of the brace of the present invention showing the reduced volume hinge.
FIG. 11 is an edge-on view of the lateral malleoli support showing the reduced volume section of the support.
FIG. 12 is a detail of the hinge member of medial malleoli support.

The invention in particular relates to a brace, including an athletic support or orthopedic brace which include an elastomeric hinge. The hinge is provided by having a ringed or looped support member that includes a section of reduced rigidity, for example, by changing the material characteristics, such as by lower cross-linking or by reducing the volume of the support for a section. In FIG. 5, the hinge section is shown at 200 and extends from an anterior edge 202 to a posterior edge 204. This section is thinner in cross section as s shown in the details shown in FIGS. 10-12. In particular, the edge-on view from FIG. 11 illustrates that the support generally stands from 0.15 0.01 to 0.15 inches, and preferably from 0.25 to 0.12, and most preferably from 0.3 to 0.8 inches or roughly 0.06 inches above the web of material, but in the hinge section 200 the thickness is from 25% to 75% and preferably from 30% to 70%, and more preferably from 40% to 60% or roughly half of that amount or 0.03 inch in thickness. Similarly, the width of the band can be reduced so long as the band remains thick enough in the hinge section that it does not become uncomfortable. In this instance, the reduced volume section is located at the bottom section of the hub so that this area will expand to allow for the hinging action of the brace. In addition, there are two malleoli supports that oppose each other and which have similar hinge sections to define the axis of rotation of the hinge assembly as an axis that extends through the supports. The hinge sections could also comprise break in the loops or notched sections, as well as thinner sections, and the band could have opposing section top and bottom at 180 degrees to allow the hinge to elongate relative to each other.

Figure 13:
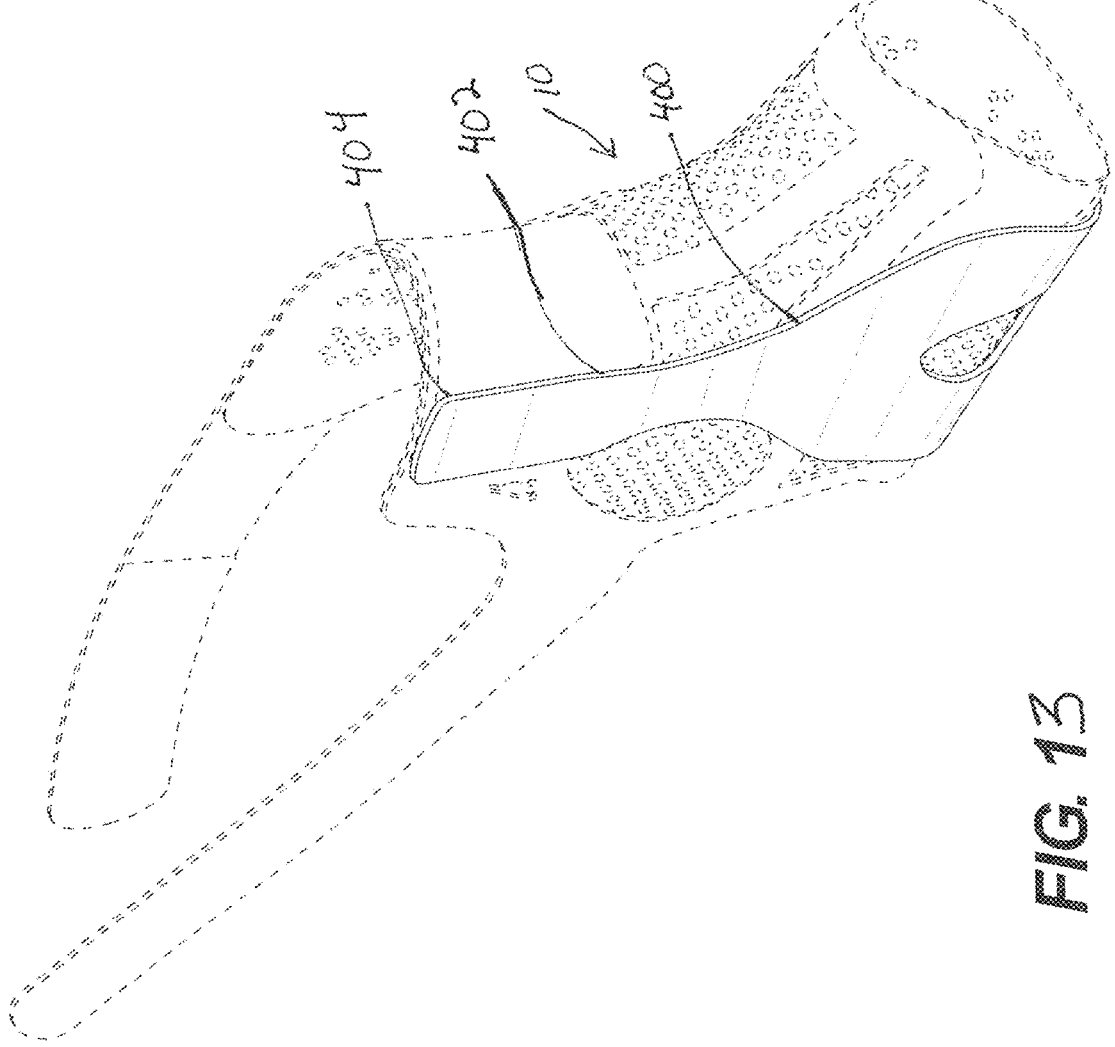
FIG. 13 is a top perspective view of a first embodiment of the present invention further including an additional supplemental lateral support.
Figure 14:
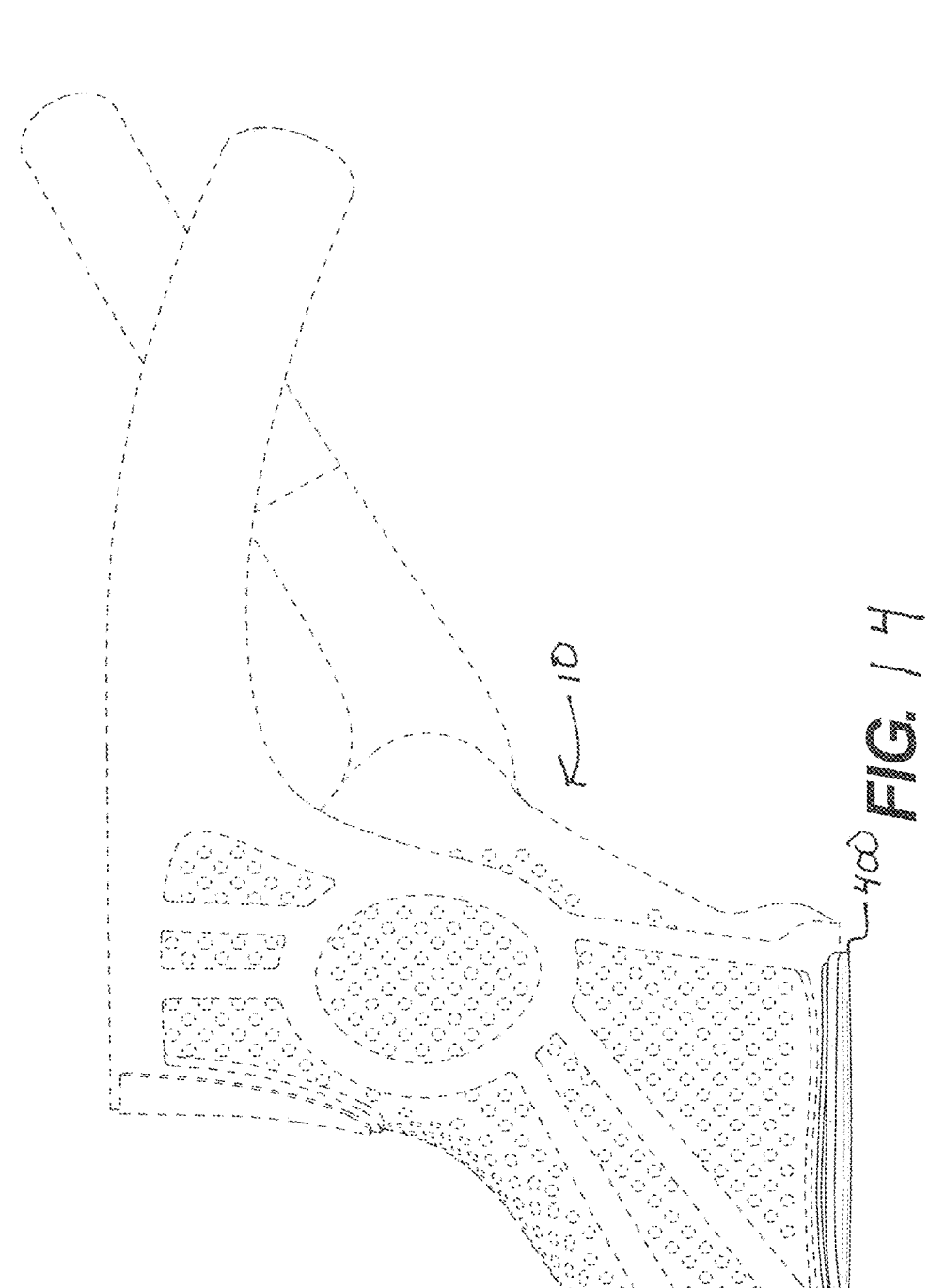
FIG. 14 is a lateral view of the embodiment of FIG. 13.
Figure 15:
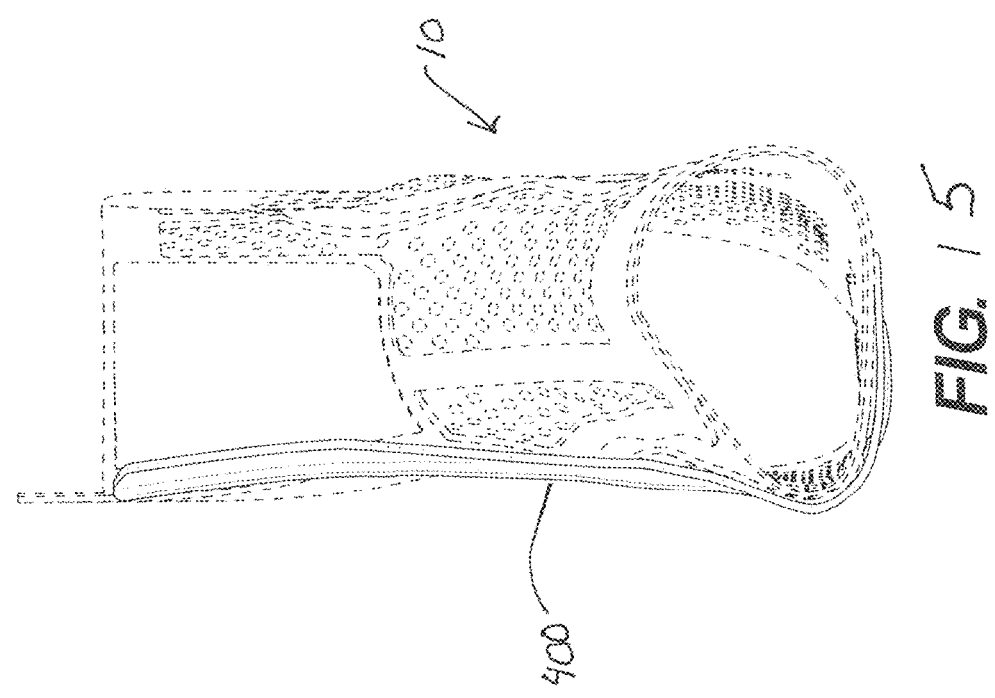
FIG. 15 is a front view of the embodiment of the brace shown in FIG. 13.
Figure 16:
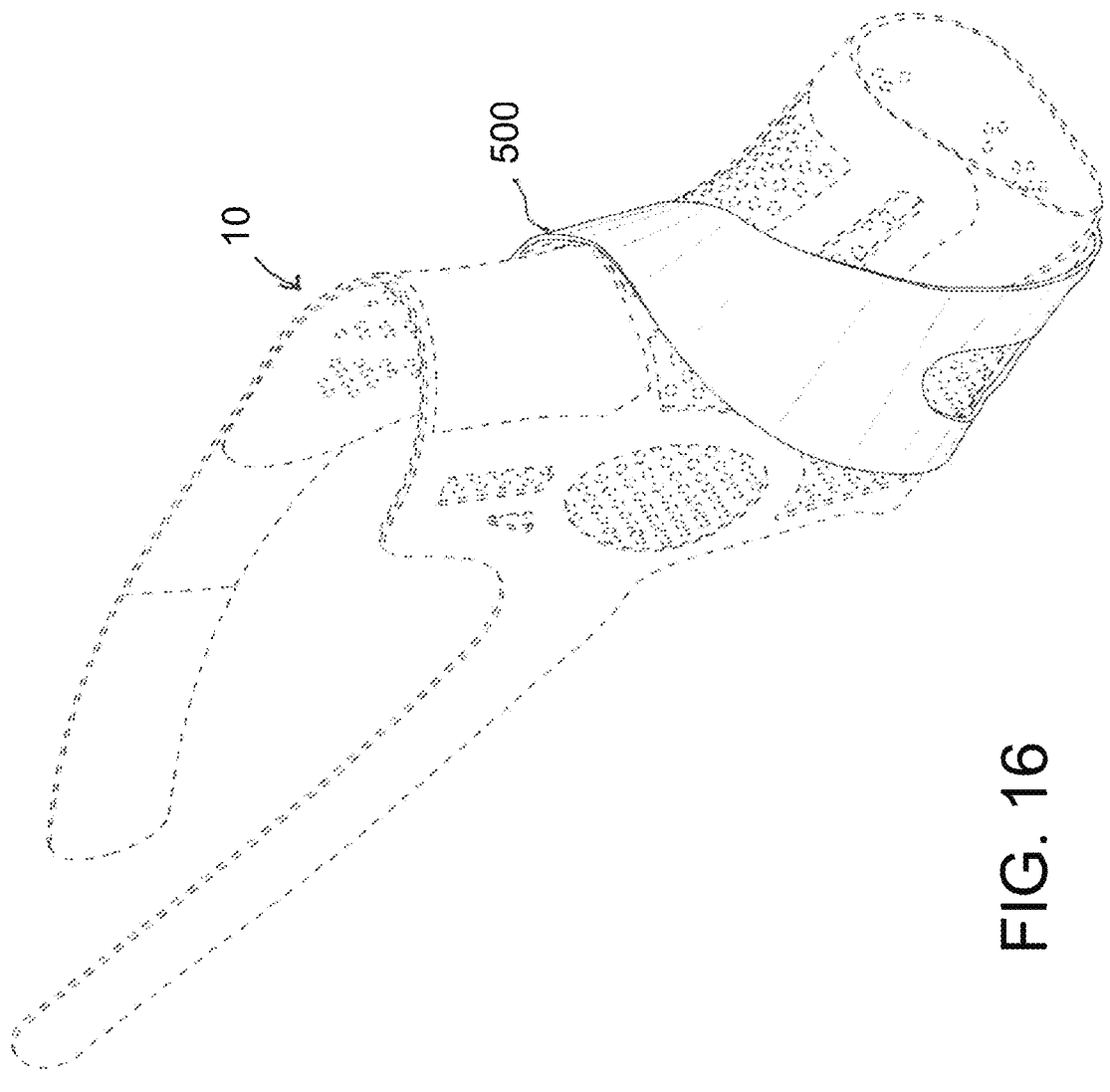
FIG. 16 is a top perspective lateral view of a second embodiment of the present invention further including the additional supplemental lateral support.
Figure 17:
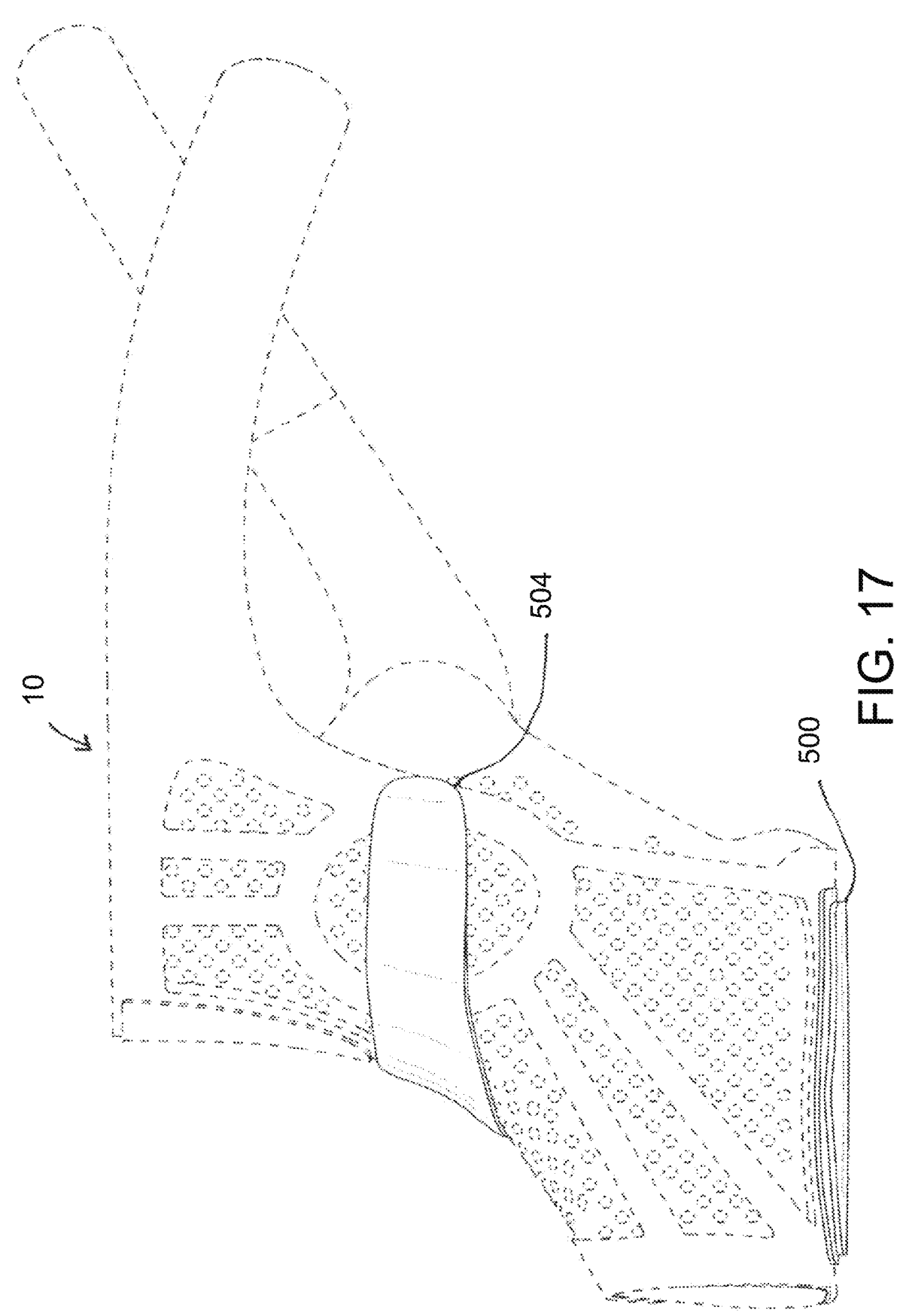
FIG. 17 is a medial view of the embodiment of FIG. 16.
Figure 18:
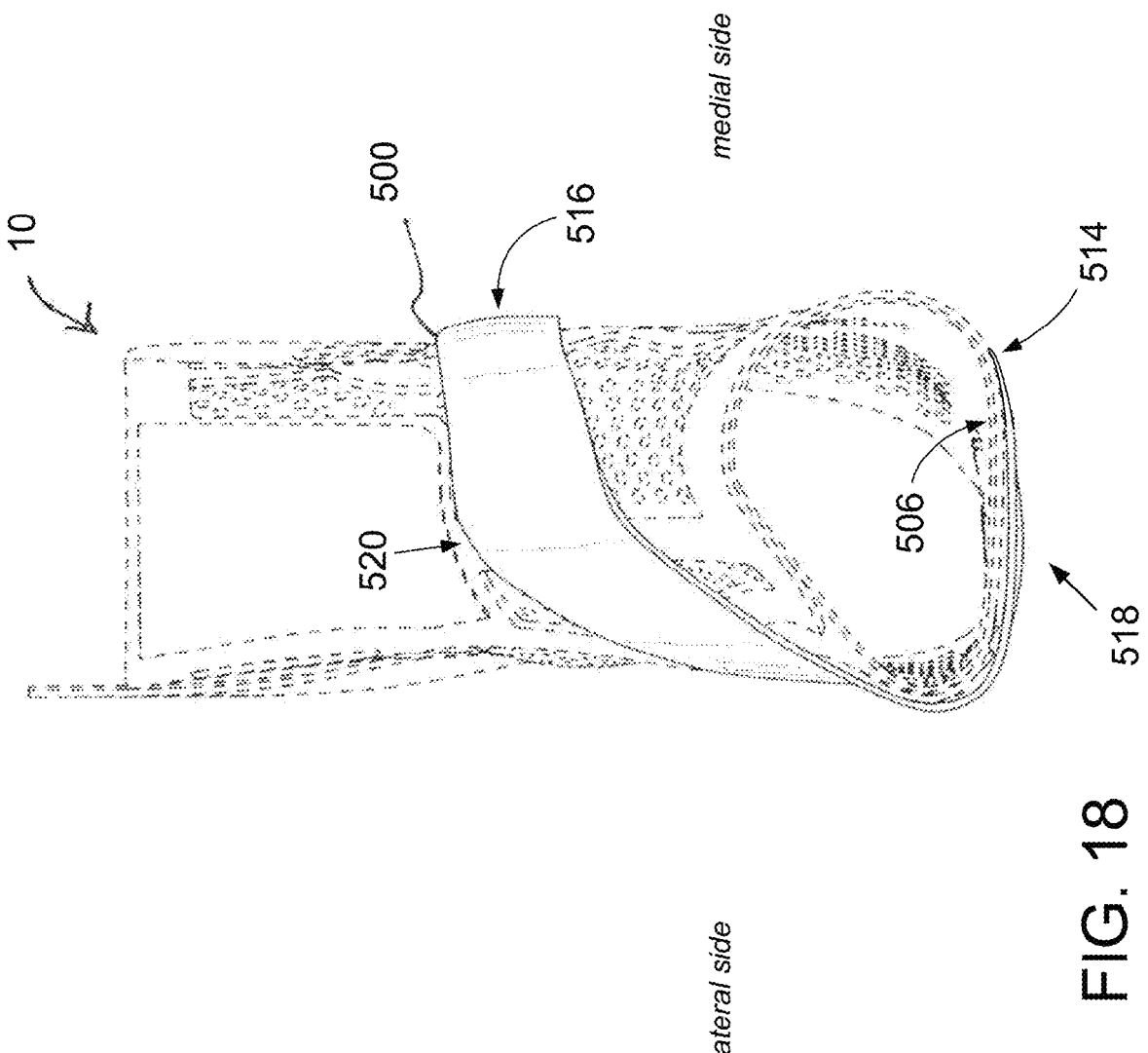
FIG. 18 is a front view of the embodiment of the brace shown in FIG. 16.
Figure 19:
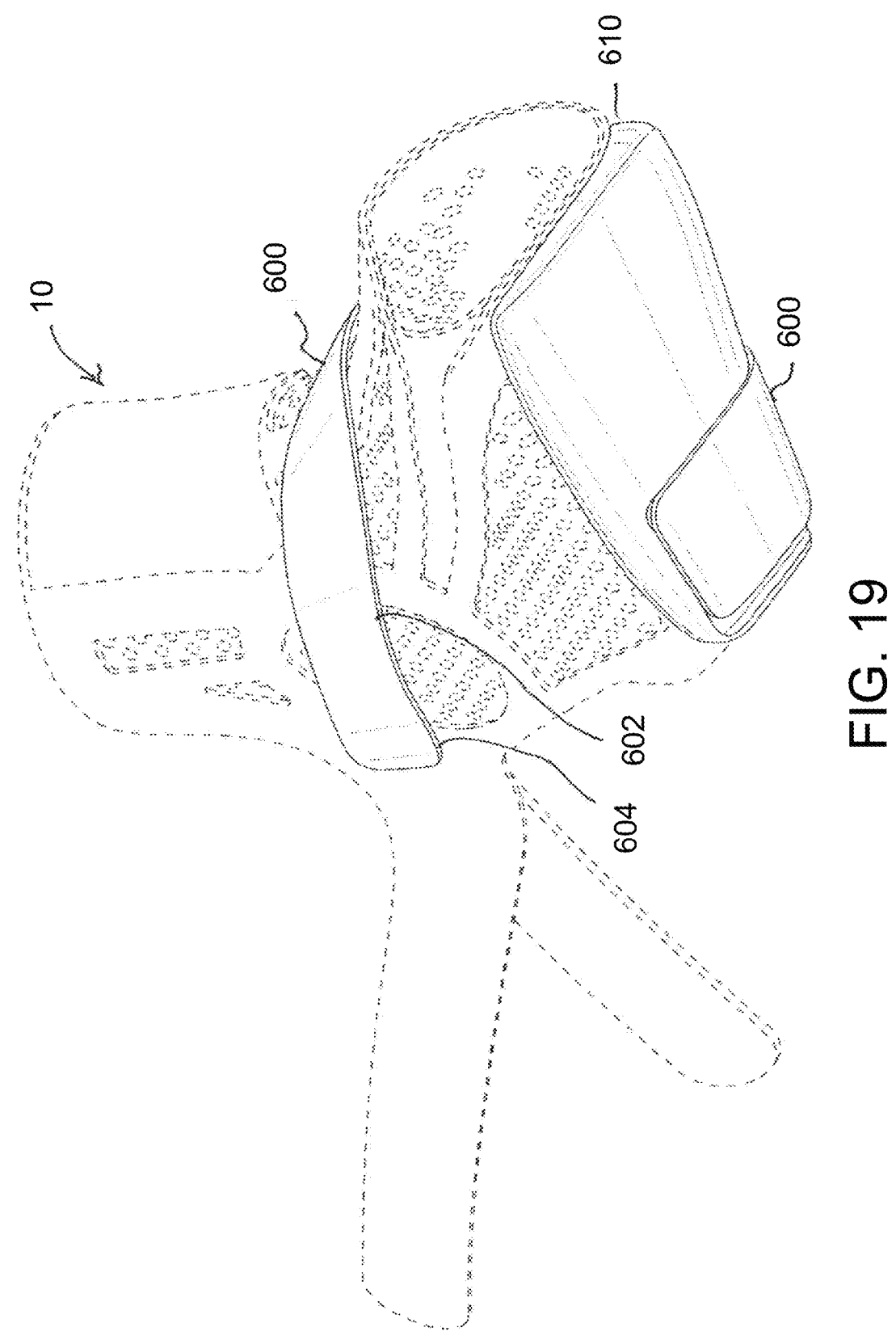
FIG. 19 is a bottom perspective lateral view of a third embodiment of the present invention further including the additional supplemental medial support and wedged footplate.
Figure 20:
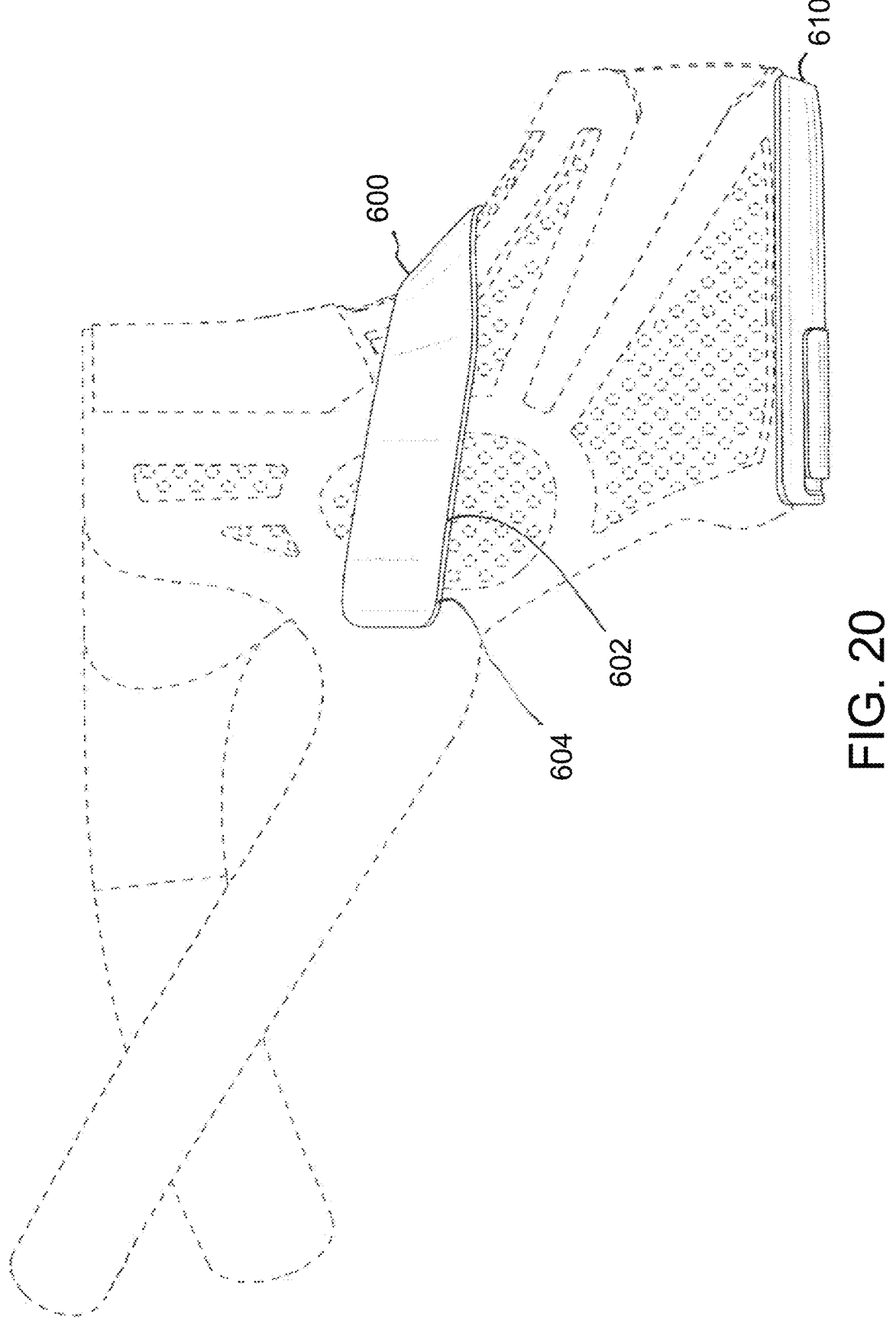
FIG. 20 is a lateral side view of the embodiment of FIG. 19.
Figure 21:
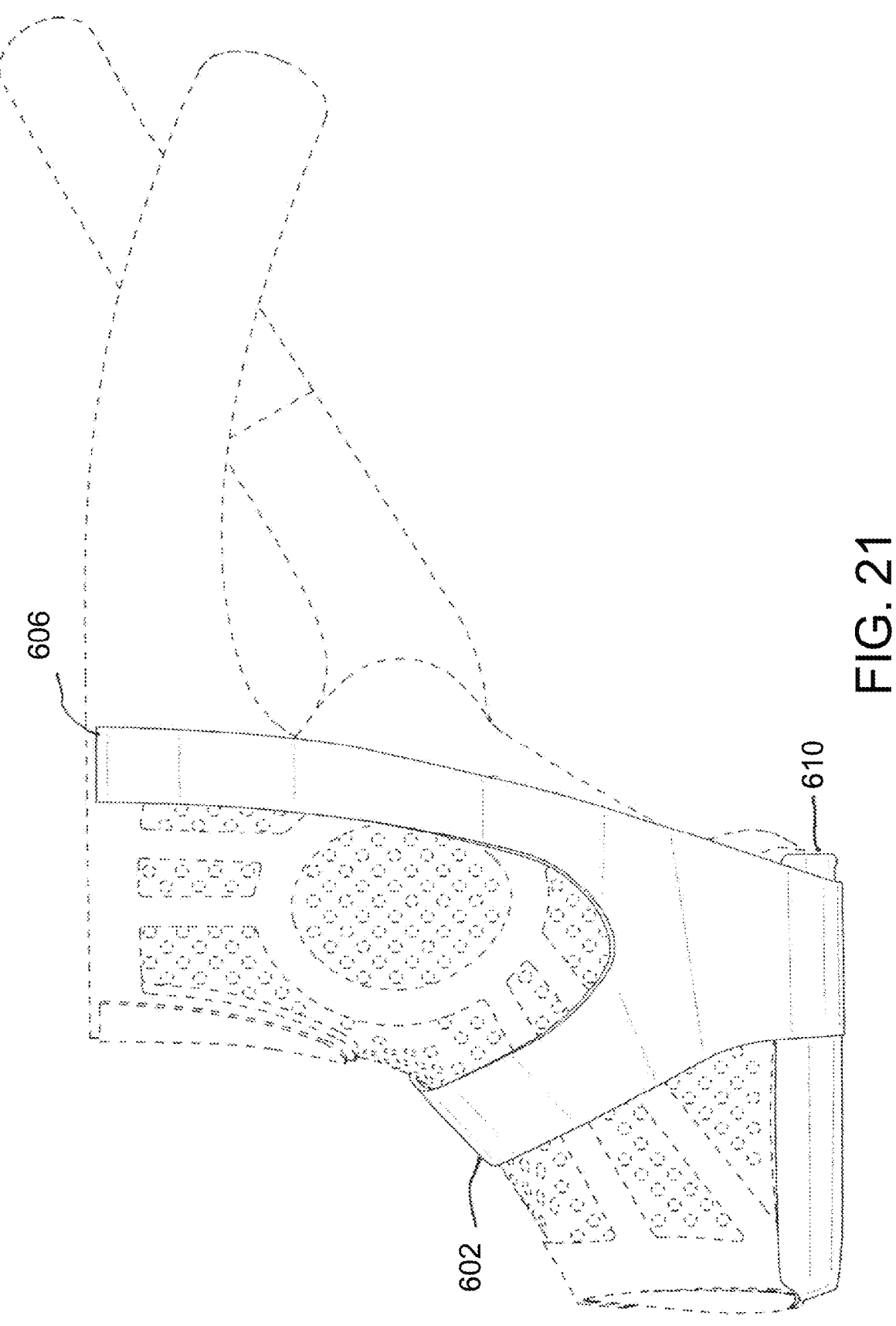
FIG. 21 is a medial side view of the embodiment of FIG. 19.
Figure 22:
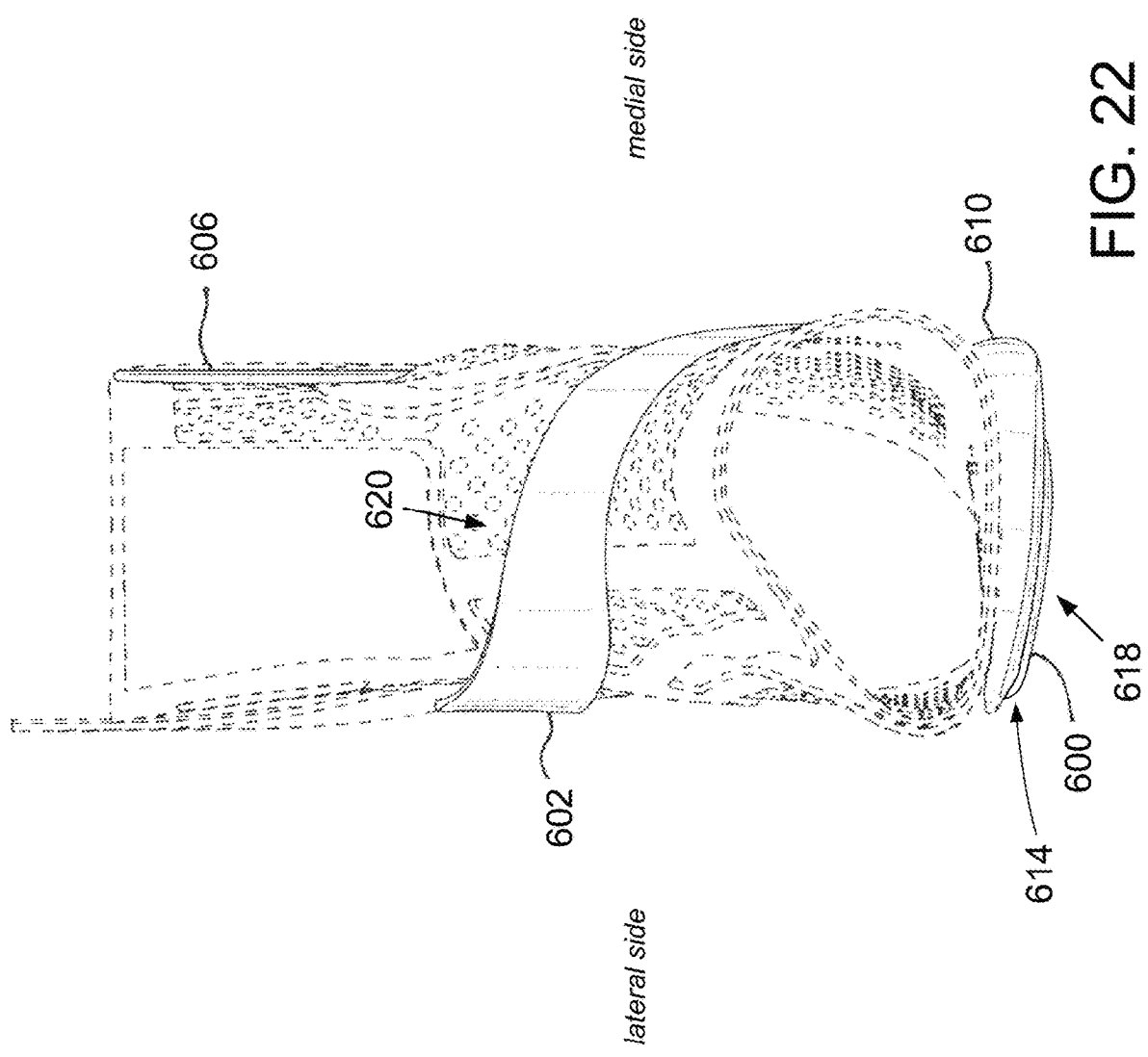
FIG. 22 is a front view of the embodiment of FIG. 19.
Figure 23:
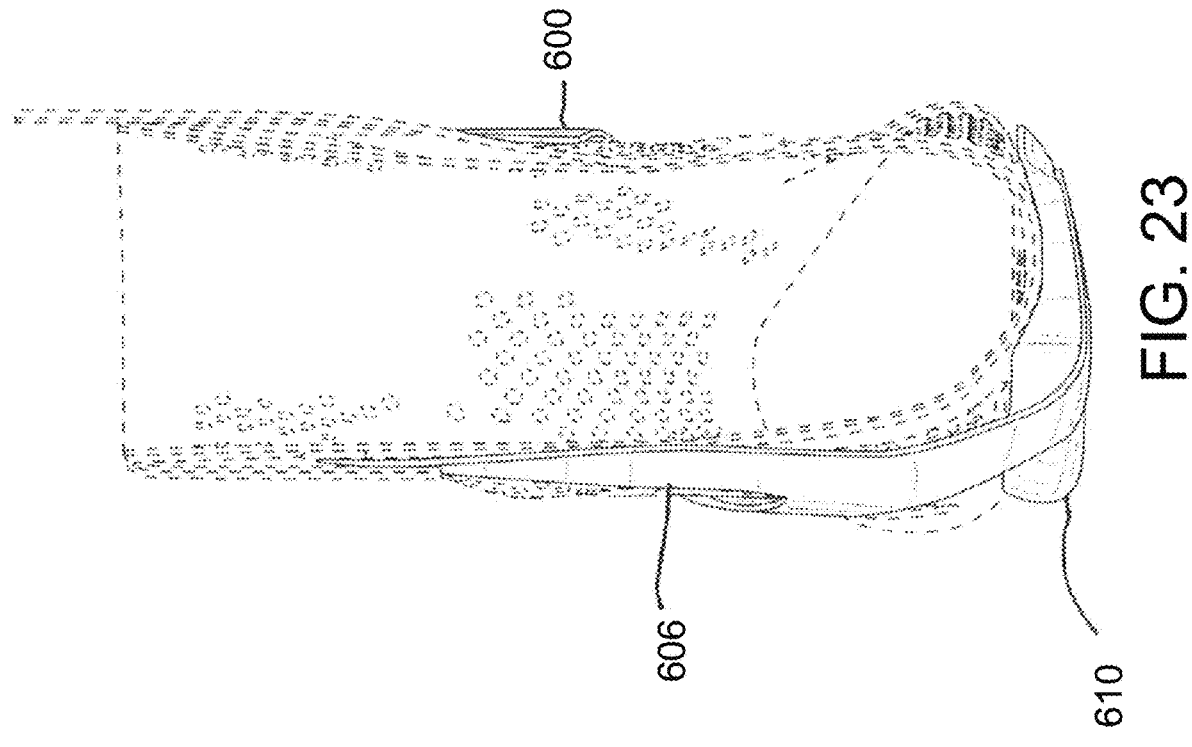
FIG. 23 is a rear view of the embodiment of FIG. 19.
Figure 24:
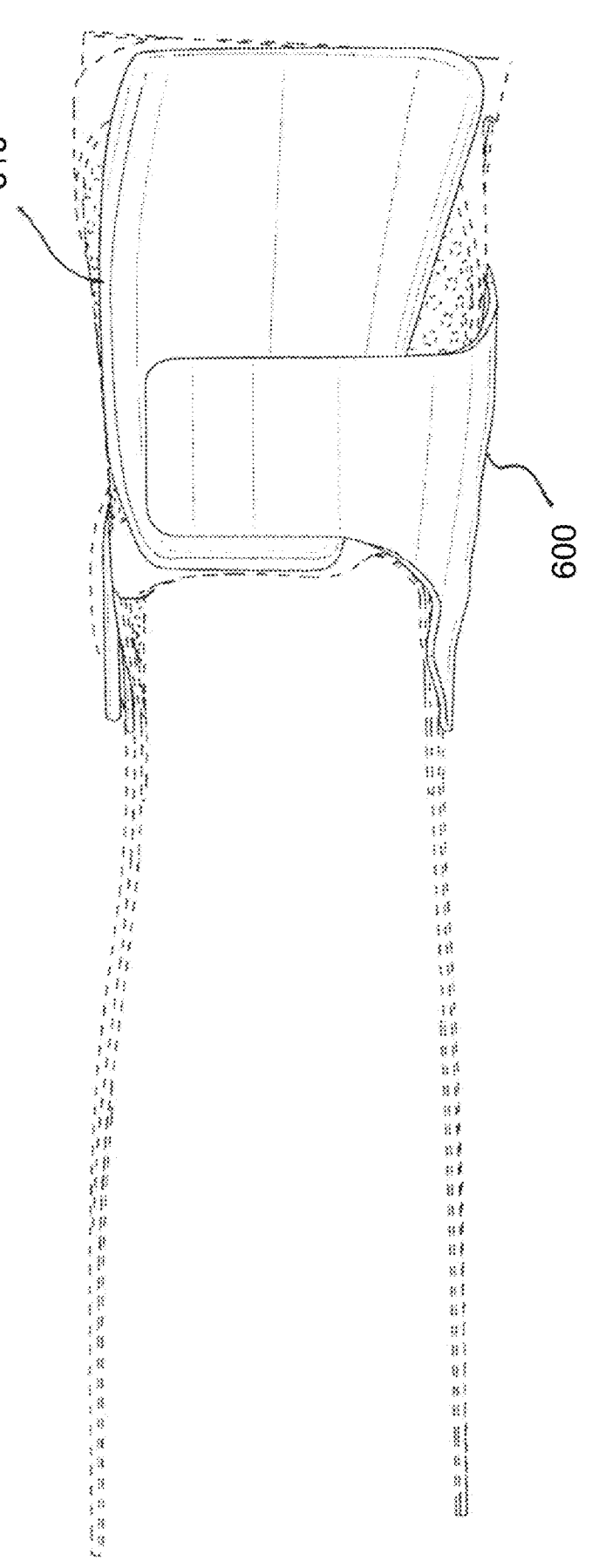
FIG. 24 is a bottom view of the embodiment of FIG. 19.
Figure 25:
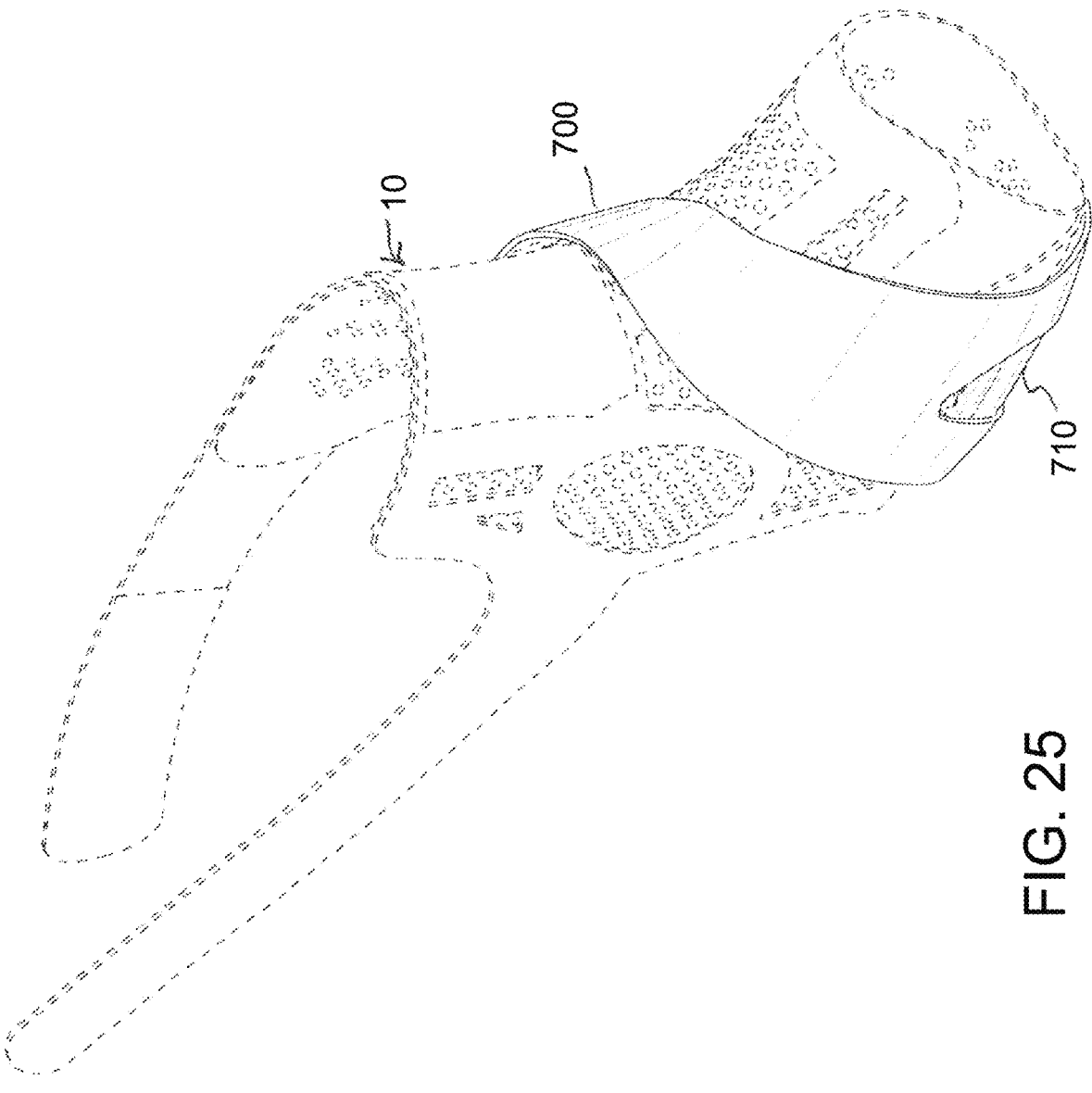
FIG. 25 is a top perspective lateral view of a fourth embodiment of the present invention further including the additional supplemental lateral support.
Figure 26:
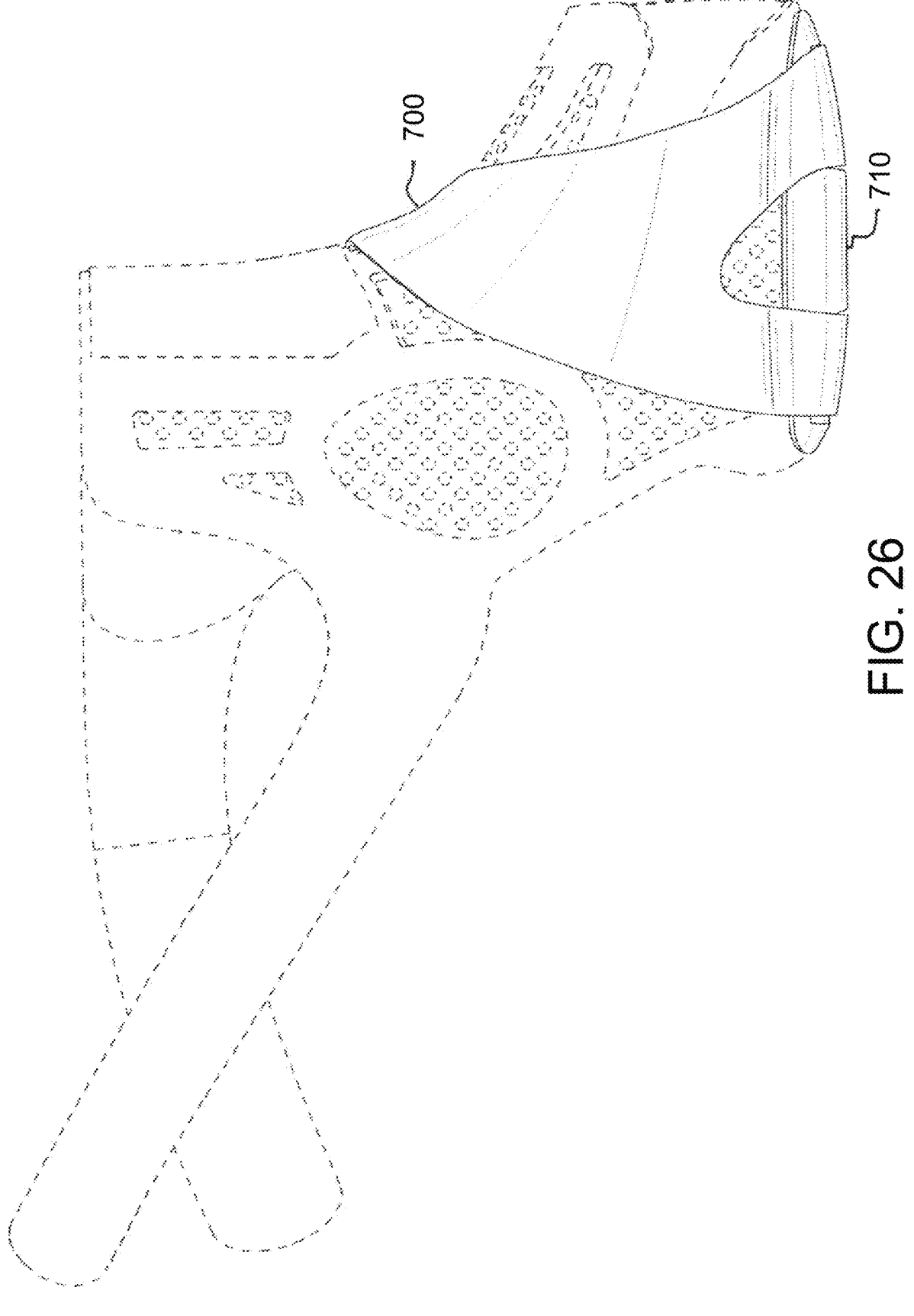
FIG. 26 is a medial view of the embodiment of FIG. 25.
Figure 27:
FIG. 27 is a medial view of the embodiment of FIG. 25.
Figure 28:
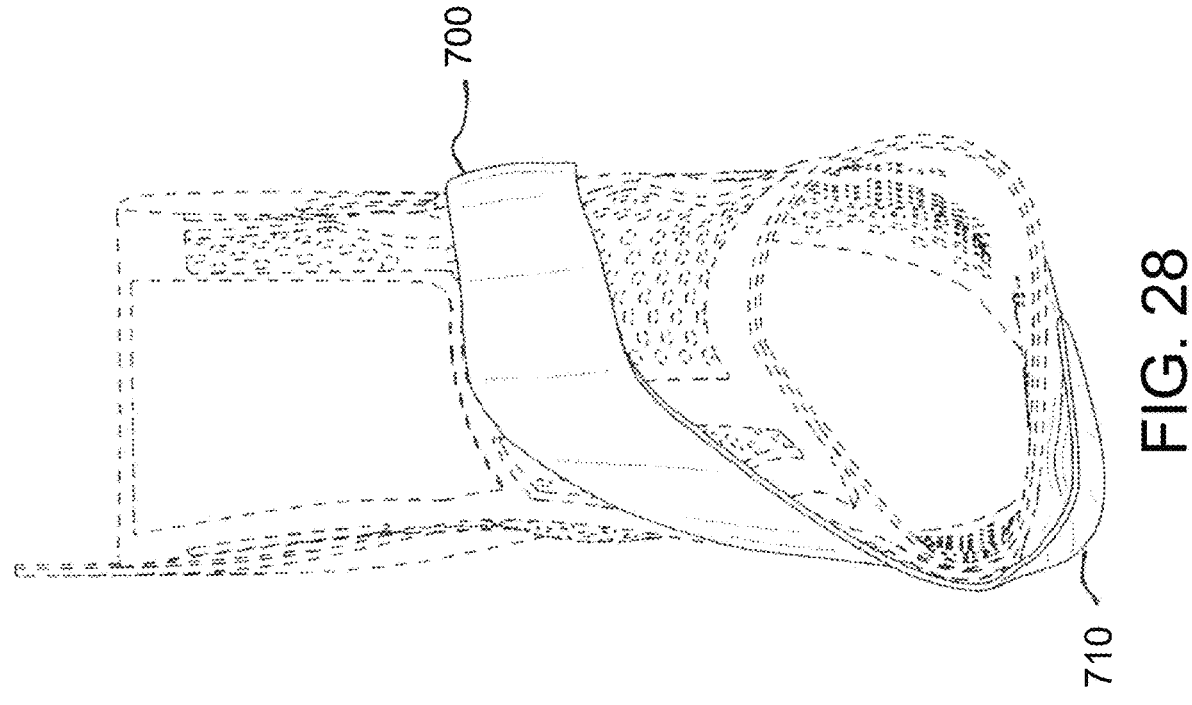
FIG. 28 is a front view of the embodiment of the brace shown in FIG. 25.

FIG. 13 illustrates a first embodiment of the brace 10 having an additional support member 400 that extends from the plantar surface of the brace where two arms members are attached, such as by Velcro to the surface and the support extends vertically upward in an arm 402 that attaches, such as by Velcro 404 to the upper side of the leg portion of the brace. FIG. 14 is a lateral view of the embodiment of FIG. 13, and FIG. 15 is a front view of the embodiment of the brace shown in FIG. 13. Another embodiment is shown in FIGS. 16 through 18, which illustrate another lateral support member 500 that again has two arms separated by an arch and that attach by Velcro to the plantar surface of the brace and further having an arm that spirals over the top of the foot to attach at a medial aspect of the brace by Velcro 504. FIG. 16 also illustrates an arched leg portion 506, arched foot portion 510, and intermediate portion 508 of the brace as well as a space or passageway indicated at 512 which is defined by these portions and in which is received a person's leg, ankle, and foot. As shown in FIG. 17, the foot strap or support member 500 has a first end 514 attached on a medial side of the brace to the arched foot portion 506; and the foot strap has a second end 516 attached on the medial side of the brace to the intermediate portion 508, the first and second ends of the foot strap both being located on the medial side of the brace. The foot strap, in its extent between the first and second ends, extends under the brace to define a plantar surface at 518 and extends up and over a front of the intermediate portion at 520. FIG. 19 through 24 illustrate an embodiment of the brace 10 having a different additional medial support member 600, which attaches to the bottom surface of a wedge plate 610 and for which an arm 602 wraps over the front of the ankle and attaches such as by Velcro 604 at the rear of the brace member, and has a second arm 606 that extends up the height of the brace. This embodiment of the brace 10 includes a Y-shaped medial support 600 which attaches to a wedge-shaped foot plate 610 that is thicker on the medial side and extends at an angle of from 2 to 10° across the width of the foot. Furthermore, as shown in FIGS. 19-24, the foot strap or support member 600 has a first end 614 attached on a lateral side of the brace to the arched foot portion by way of the wedge plate 610; and the foot strap has a second end 616 located on the lateral side of the brace, the first and second ends of the foot strap both being located on the lateral side of the brace. The foot strap, in its extent between the first and second ends, extends under the brace to define a plantar surface at 618 and extends up and over a front of the intermediate portion at 620. In a fourth embodiment of the invention illustrated FIGS. 25-28, the brace support assembly includes a strap 700 and wedge foot plate 710 which is thicker on the lateral side of the foot and angle to a narrower thickness across the foot, also at an angle of from 2 to 10° across the width of the foot, but in the opposite direction. The strap extends across the top of the foot and fastens on the brace 10, such as by Velcro and the footplate 710 is attached to the planar surface of the brace, such as by Velcro, and the strap is held to the bottom surface of the footplate such as by Velcro, and in fact, the footplate preferably includes recesses so that the strap is flush to the bottom of the footplate. Furthermore, as shown in FIGS. 25-28, the foot strap 700 has a first end 714 attached on a medial side of the brace is attached to the foot portion by way of the wedge plate 710; and the foot strap has a second end 716 located on the medial side of the brace, the first and second ends of the foot strap both being located on the medial side of the brace. The foot strap, in its extent between the first and second ends, extends under the brace to define a plantar surface at 718 and extends up and over a front of the intermediate portion at 720.

While in accordance with the patent statutes the best mode and preferred embodiment have been set forth, the scope of the invention is not limited thereto but rather by the scope of the attached claims.

What is claimed is:

1. A method of donning a rear-entry ankle brace, the brace comprising, an elastomeric component comprising a distal end portion, a proximal end portion, and an intermediate portion, wherein the proximal end portion defines a leg opening for rear entry of the brace, leg straps for adjustably tensioning the proximal end portion, each of said leg straps extending from a respective rear edge of the leg opening, and a foot strap having a first end attached on a medial side of the brace to the distal end portion for adjustably tensioning the distal end portion, the method comprising the steps of:

(a) positioning the rear-entry ankle brace on a mid-foot and a lower portion of a leg so as to span an ankle joint, with the distal end portion extending over and covering a top and medial and lateral sides of the mid-foot, and with the proximal end extending over and covering a front and medial and lateral sides of the lower portion of the leg;

(b) tensioning the leg straps for closing the leg opening and securing the leg straps in tension by attaching the leg straps on a front of the brace; and (c) extending the foot strap from the first end under the brace so as to define a plantar surface of the brace and further extending the foot strap over a front of the intermediate portion to the medial side of the brace for attaching a second end of the foot strap on the medial side of the brace, whereby the first and second ends of the foot strap are both located on the medial side of the brace.

2. The method of claim 1, wherein the elastomeric component further defines, on the medial side of the brace, a central hub with radiating struts that extend from the central hub and with interstitial areas extending between the radiating struts; and wherein the foot strap extends over the central hub.

3. The method of claim 2, wherein the interstitial areas comprise areas that are substantially thinner than the radiating struts and that include perforations extending through the elastomeric component for breathability of the brace when worn.

4. The method of claim 2, wherein the second end of the foot strap is configured to be secured in tension at the central hub.

5. The method of claim 2, wherein each of a plurality of the radiating struts extends on the medial side of the brace from the central hub to the proximal edge of the proximal portion.

6. The method of claim 2, wherein each of a plurality of the radiating struts extends on the medial side of the brace from the central hub to a distal edge of the distal portion.

7. The method of claim 1, wherein the distal end portion is positioned so as to extend below the foot of the wearer.

8. The method of claim 1, wherein the distal end portion is positioned so as to entirely encircle the foot of the wearer.

9. The method of claim 1, wherein the elastomeric component consists of a single molded piece of one or more thermoplastic materials.

10. The method of claim 1, further comprising using hook-and-loop fasteners to secure the second end of the foot strap in tension on the medial side of the brace.

11. A method of donning a rear-entry ankle brace, the brace comprising, an elastomeric component comprising a distal end portion, a proximal end portion, and an intermediate portion, wherein the proximal end portion defines a leg opening for rear entry of the brace, leg straps for adjustably tensioning the proximal end portion, each of said leg straps extending from a respective rear edge of the leg opening, and a foot strap having a first end attached on a lateral side of the brace to the distal end portion for adjustably tensioning the distal end portion, the method comprising the steps of: (a) positioning the rear-entry ankle brace on a mid-foot and a lower portion of a leg so as to span an ankle joint, with the distal end portion extending over and covering a top and medial and lateral sides of the mid-foot, and with the proximal end extending over and covering a front and medial and lateral sides of the lower portion of the leg; (b) tensioning the leg straps for closing the leg opening and securing the leg straps in tension by attaching the leg straps on a front of the brace; and (c) extending the foot strap from the first end under the brace so as to define a plantar surface of the brace and further extending the foot strap over a front of the intermediate portion to the lateral side of the brace for attaching a second end of the foot strap on the lateral side of the brace, whereby the first and second ends of the foot strap are both located on the lateral side of the brace.

12. The method of claim 11, wherein the elastomeric component further defines, on the lateral side of the brace, a central hub with radiating struts that extend from the central hub and with interstitial areas extending between the radiating struts; and wherein the foot strap extends over the central hub.

13. The method of claim 12, wherein the interstitial areas comprise areas that are substantially thinner than the radiating struts and that include perforations extending through the elastomeric component for breathability of the brace when worn.

14. The method of claim 12, wherein the second end of the foot strap is configured to be secured in tension at the central hub.

15. The method of claim 12, wherein each of a plurality of the radiating struts extends on the lateral side of the brace from the central hub to the proximal edge of the proximal portion.

16. The method of claim 12, wherein each of a plurality of the radiating struts extends on the lateral side of the brace from the central hub to a distal edge of the distal portion.

17. The method of claim 11, wherein the distal end portion is positioned so as to extend below the foot of the wearer.

18. The method of claim 11, wherein the distal end portion is positioned so as to entirely encircle the foot of the wearer.

19. The method of claim 11, wherein the elastomeric component consists of a single molded piece of one or more thermoplastic materials.

20. The method of claim 11, further comprising using hook-and-loop fasteners to secure the second end of the foot strap in tension on the lateral side of the brace.

* * * * *